United States Patent
Xu et al.

(10) Patent No.: US 10,653,815 B2
(45) Date of Patent: May 19, 2020

(54) MESH COMPOSITIONS AND METHODS OF PRODUCTION

(71) Applicant: LifeCell Corporation, Branchburg, NJ (US)

(72) Inventors: Hui Xu, Plainsboro, NJ (US); Sean Collins, Valley Cottage, NY (US); Li Ting Huang, Branchburg, NJ (US); Hua Wan, Princeton, NJ (US); Yi Chen, Lawrenceville, NJ (US)

(73) Assignee: LifeCell Corporation, Madison, NJ (US)

( * ) Notice: Subject to any disclaimer, the term of this patent is extended or adjusted under 35 U.S.C. 154(b) by 264 days.

(21) Appl. No.: 15/618,341

(22) Filed: Jun. 9, 2017

(65) Prior Publication Data

US 2017/0354759 A1 Dec. 14, 2017

Related U.S. Application Data

(60) Provisional application No. 62/347,686, filed on Jun. 9, 2016.

(51) Int. Cl.
*A61L 27/24* (2006.01)
*A61L 27/36* (2006.01)
*A61L 27/54* (2006.01)
*A61L 27/56* (2006.01)

(52) U.S. Cl.
CPC ............ *A61L 27/24* (2013.01); *A61L 27/3604* (2013.01); *A61L 27/3683* (2013.01); *A61L 27/54* (2013.01); *A61L 27/56* (2013.01); *A61L 2300/404* (2013.01); *A61L 2300/41* (2013.01); *A61L 2430/34* (2013.01)

(58) Field of Classification Search
None
See application file for complete search history.

(56) References Cited

U.S. PATENT DOCUMENTS

| 2010/0272782 A1* | 10/2010 | Owens | A61L 31/005 424/443 |
| 2013/0158658 A1* | 6/2013 | Hayzlett | A61F 2/02 623/8 |

FOREIGN PATENT DOCUMENTS

| WO | 03/007790 A2 | 1/2003 |
| WO | 2008/134541 A2 | 11/2008 |
| WO | 2009/009620 A2 | 1/2009 |
| WO | 2013/070881 A1 | 5/2013 |

OTHER PUBLICATIONS

Bowes, Joane H., and R. H. Kenten. "The swelling of collagen in alkaline solutions. 1. Swelling in solutions of sodium hydroxide." Biochemical Journal 46.1 (1950): 1-8.*
Badylak, Stephen F., Donald O. Freytes, and Thomas W. Gilbert. "Extracellular matrix as a biological scaffold material: structure and function." Acta biomaterialia 5.1 (2009): 1-13.*
Chen, Ying-Chen, et al. "Development and characterization of acellular extracellular matrix scaffolds from porcine menisci for use in cartilage tissue engineering." Tissue Engineering Part C: Methods 21.9 (2015): 971-986.*
Dong, Xiaochao, et al. "RGD-modified acellular bovine pericardium as a bioprosthetic scaffold for tissue engineering." Journal of Materials Science: Materials in Medicine 20.11 (2009): 2327-2336.*
Gilbert, Thomas W., Tiffany L. Sellaro, and Stephen F. Badylak. "Decellularization of tissues and organs." Biomaterials 27.19 (2006): 3675-3683.*
Reing, Janet E., et al. "The effects of processing methods upon mechanical and biologic properties of porcine dermal extracellular matrix scaffolds." Biomaterials 31.33 (2010): 8626-8633.*
International Search Report and Written Opinion for PCT/US2017/036708 dated Sep. 1, 2017, pp. 1-16.

* cited by examiner

*Primary Examiner* — Bethany P Barham
*Assistant Examiner* — Peter Anthropolos
(74) *Attorney, Agent, or Firm* — McCarter & English, LLP; Matthew R. Van Eman

(57) ABSTRACT

Methods of forming a composition for treatment, compositions for treatment, and methods of treatment with the compositions are provided. The methods can include coating a synthetic material substrate with a biologic material. A portion of the biologic material can be acid-swelled.

19 Claims, 25 Drawing Sheets

```
Pre-process biologic material                              ─100
            │
            ▼
Reduce particle size of biologic material                   ─102
            │
            ▼
Process size reduced biologic material                      ─104
            │
            ▼
Prepare slurry with biologic material                       ─106
            │
            ▼
Incorporate biologic material into synthetic material       ─108
            │
            ▼
Freeze dry composition                                      ─110
            │
            ▼
Stabilize composition                                       ─112
            │
            ▼
Compress composition                                        ─114
            │
            ▼
Stabilize compressed composition                            ─116
            │
            ▼
Add surface coating to compressed composition               ─118
```

FIG. 1

MESH COMPOSITIONS AND METHODS OF PRODUCTION

This application claims the benefit under 35 USC § 119 of commonly assigned U.S. Provisional Patent Application No. 62/347,686, filed on Jun. 9, 2016. The entire content of the foregoing provisional patent application is incorporated herein by reference.

The present disclosure relates to compositions and methods of treatment, and more particularly, to coated mesh compositions and methods of production of compositions for treatment in accordance with the methods.

Biologic materials have been used for regeneration, reinforcement, or repair of defective or damaged tissues (e.g., hernia repair, abdominal wall repair, breast reconstruction, connective tissue regeneration, tendon or ligament treatment, or combinations thereof). Compared with synthetics, biologic materials can provide lower risks of rejection, complications, and infections, while allowing regeneration of normal tissue architecture and function. The expense associated with biologic materials, however, can increases the overall cost of surgical procedures. And although certain biologic materials are incredibly strong and effective, there remains a need for materials having even greater strength and long-term structural support.

Synthetic materials are also effective for some applications. Synthetic materials can provide strength, lower cost, ready availability, uniformity, biocompatibility, flexibility, and resistance to acids, stress, and cracking. Synthetic materials, however, can trigger an inflammatory response that can lead to a larger degree of scar tissue formation or other complications. In addition, synthetics may not support tissue regeneration.

Devices that incorporate the advantages of both synthetic and biologic materials are desirable for some applications. To ensure a strong and effective treatment, however, it may be desirable to use a composition that provides a stronger attachment or engagement between the biocompatible and synthetic materials, resulting in a composition that reduces or prevents separation between the biologic and synthetic materials. Accordingly, methods of treatment including compositions, as well as compositions used in the methods, are provided.

According to certain embodiments, a method of producing a surgical material (e.g., a composition) for treatment is provided. The method can include providing a synthetic material substrate and providing a collagen-containing tissue matrix (e.g., a biologic material). The method can include creating a slurry with the collagen-containing tissue matrix. Creating the slurry can include subjecting a portion of the collagen-containing tissue matrix to an acid-swelling process to produce an acid-swelled tissue matrix. Creating the slurry can include mixing the acid-swelled tissue matrix with the collagen-containing tissue matrix to produce a slurry having between approximately 5% and approximately 35% by volume of the collagen-containing tissue matrix in the slurry as the acid-swelled tissue matrix. The method can include embedding the synthetic material substrate in the slurry. In certain embodiments, the slurry can have between, e.g., approximately 5% and approximately 25%, approximately 5% and approximately 15%, or approximately 5% and approximately 10%, by volume of the collagen-containing tissue matrix in the slurry as the acid-swelled tissue matrix.

In certain embodiments, the method can include processing the collagen-containing tissue matrix to reduce a particle size to produce a group of collagen-containing tissue matrix fragments. At least a portion of the group of collagen-containing tissue matrix fragments can include frayed ends. In certain embodiments, the acid swelling process can include suspending the collagen-containing tissue matrix in acid and incubating the collagen-containing tissue matrix in the acid until swelling occurs. The acid can be at least one of acetic acid, ascorbic acid, boric acid, carbonic acid, citric acid, hydrochloric acid, lactic acid, tannic acid, phosphoric acid, and sulfuric acid. In certain embodiments, the method can include rubbing or mechanically moving the collagen-containing tissue matrix slurry into the synthetic material substrate. In certain embodiments, the method can include freeze drying the synthetic material substrate and at least a portion of the slurry to form the surgical material. Freeze drying the synthetic material substrate and at least the portion of the slurry can produce a smooth layer or skin on an outer surface of the surgical material.

Increasing a percentage by volume of the acid-swelled collagen-containing tissue matrix in the slurry can increase the stiffness of the surgical material. The method can include performing a decellularization process for the collagen-containing tissue matrix. The method can include resuspending the slurry in a buffer. The method can include incorporating an antimicrobial compound (e.g., chlorehexidine, silver, citric acid, triple antibiotic, or tetracycline) into the surgical material. The method can include incorporating an anti-inflammatory compound into the surgical material.

The synthetic material substrate can have a variety of different shapes or configurations. In certain embodiments, the synthetic material substrate can include at least one of a porous foam, a planar mesh, a multifilament woven material, a monofilament woven material, multi-leveled layers, or multi-directional layers. A tensile strength of the synthetic material substrate can be greater than a tensile strength of the collagen-containing tissue matrix. The synthetic material substrate can be biocompatible. The synthetic material substrate can include at least one of polypropylene, polytetrafluoroethylene, polyester, terephthalate, polyglycolide, or poly-4-hydroxybutyrate. The synthetic material substrate can include one or more textured surfaces.

In certain embodiments, the collagen-containing tissue matrix can include an acellular tissue matrix. In certain embodiments, the collagen-containing tissue matrix can include an acellular dermal matrix. In certain embodiments, the collagen-containing tissue matrix can include a porcine tissue matrix.

In certain embodiments, the method can include pouring a portion of the slurry into a mold to cover a bottom of the mold with the slurry. As used herein, the term "mold" will be understood to refer to any container or housing into which the biologic and synthetic materials are positioned for forming the exemplary compositions or surgical materials. The method can include positioning the synthetic material substrate coated with the slurry into the mold on top of the slurry. The method can include pouring the slurry over the synthetic material substrate positioned in the mold to cover the synthetic material substrate. In certain embodiments, the method can include freeze drying the surgical material to combine the collagen-containing tissue matrix and the synthetic material substrate. In certain embodiments, the method can include freeze drying the synthetic material substrate and at least a portion of the slurry to form the surgical material. Freeze drying the synthetic material substrate and at least a portion of the slurry produces a smooth layer or skin on an outer surface of the surgical material.

According to certain embodiments, a composition for treatment is provided. The composition can include a synthetic material substrate and a collagen-containing tissue matrix (e.g., a biologic material) embedded to, attached to, coating, encapsulating, encasing or covering the synthetic material substrate. The collagen-containing tissue matrix can be in the form of a dried sponge that prior to drying included between, e.g., approximately 5% and approximately 35%, approximately 5% and approximately 25%, approximately 5% and approximately 15%, or approximately 5% and approximately 10%, by volume of the collagen-containing tissue matrix slurry subjected to an acid-swelling process.

In certain embodiments, the collagen-containing tissue matrix can include a group of collagen-containing tissue matrix fragments (e.g., a reduced particle size as compared to the collagen-containing tissue matrix). At least a portion of the group of collagen-containing tissue matrix fragments can include frayed ends. In certain embodiments, the slurry can be rubbed or mechanically moved into the synthetic material substrate. In certain embodiments, the synthetic material substrate and at least a portion of the slurry can be freeze dried to form a surgical material or composition. Freeze drying the synthetic material substrate and at least the portion of the slurry can produce a smooth layer or skin on an outer surface of the composition. In certain embodiments, the composition can be compressed after freeze drying.

In certain embodiments, the composition can include an antimicrobial compound. In certain embodiments, the composition can include an anti-inflammatory compound. The synthetic material substrate can define a three-dimensional form. In certain embodiments, the synthetic material substrate can include at least one of a porous foam, a planar mesh, a monofilament woven material, a multifilament woven material, multi-leveled layers, or multi-directional layers. A biomechanical strength of the synthetic material substrate can be greater than a biomechanical strength of the collagen-containing tissue matrix. The synthetic material substrate can be biocompatible. The synthetic material substrate can include at least one of polypropylene, polytetrafluoroethylene, polyester, terephthalate, polyglycolide, poly-4-hydroxybutyrate, or combinations thereof.

In certain embodiments, the synthetic material substrate can include one or more textured surfaces. The collagen-containing tissue matrix can include an acellular tissue matrix. The collagen-containing tissue matrix can include an acellular dermal matrix. The collagen-containing tissue matrix can include a porcine tissue matrix. The synthetic material substrate and the dried slurry can form a combined structure. In certain embodiments, at least a portion of the dried slurry can include a smooth layer or skin on an outer surface of the composition. In certain embodiments, the composition can be compressed to reduce the overall thickness of the composition.

According to certain embodiments, a method of treatment is provided. The method can include selecting an anatomic site and implanting in or on the anatomic site a composition as described above. The composition can promote tissue ingrowth with tissue surrounding the anatomic site. The composition can reduce inflammation at the anatomic site as compared to a synthetic material substrate without the tissue matrix.

According to certain embodiments, a method of forming a composition for treatment is provided. The method can include providing a synthetic material substrate and a biologic material. The method can include processing the biologic material to reduce a particle size of the biologic material to form a group of biologic material fragments. At least a portion of the group of biologic material fragments can include frayed ends. In certain embodiments, the method can include coating or mixing the fragments with an anti-inflammatory agent. The method can include creating a biologic material slurry with the group of biologic material fragments. The method can include encasing, covering, or coating at least a portion of the synthetic material substrate with the biologic material slurry. In certain embodiments, the method can include causing interlocking of the frayed ends of the biologic material fragments to strengthen the attachment of the biologic material to the synthetic material substrate. Interlocking the frayed ends of the biologic material fragments can also strengthen the attachment of the biologic material to each other to increase the integrity of the resulting hybrid composition.

According to certain embodiments, a composition for treatment is provided. The composition can include a synthetic material substrate and a biologic material encasing, attached, or embedded to the synthetic material substrate. The biologic material can be in the form of a dried sponge including a group of biologic material fragments, at least a portion of the group of biologic material fragments including frayed ends. Prior to drying, the slurry can be coated over at least a portion of the synthetic material substrate to encase the synthetic material substrate.

According to certain embodiments, a method of treatment is provided. The method can include selecting an anatomic site and implanting in or on the anatomic site a composition described herein.

According to certain embodiments, a method of forming a composition for treatment is provided. The method can include providing a synthetic material substrate and a biologic material. The method can include creating a biologic material slurry with the biologic material. The method can include covering or coating at least a portion of the synthetic material substrate with the biologic material slurry. The method can include rubbing or mechanically moving the biologic material slurry into the synthetic material substrate. In certain embodiments, the method can include freeze drying and compressing the composition. Compressing the composition can, e.g., reduce a thickness of the biologic material layer covering or coating the synthetic material substrate, increase a density of the biologic material layer covering or coating the synthetic material substrate, and strengthen a structural stability of the biologic material.

According to certain embodiments, a composition for treatment is provided. The composition can include a synthetic material substrate and a biologic material attached to the synthetic material substrate. The biologic material can be in the form of a dried slurry (or sponge) covering and compressed against the synthetic material substrate. Compression of the slurry after drying (e.g., freeze drying or air drying) can assist in attaching the biologic material to the synthetic material substrate.

According to certain embodiments, a method of treatment is provided. The method can include selecting an anatomic site and implanting in or on the anatomic site a composition.

According to certain embodiments, a method of forming a composition for treatment is provided. The method can include providing a synthetic material substrate and a biologic material. The method can include creating a biologic material slurry with the biologic material. The method can include covering or coating at least a portion of the synthetic material substrate with the biologic material slurry. The method can include freeze drying the synthetic material substrate and at least a portion of the biologic material slurry to form a composition. Freeze drying the synthetic material substrate and at least the portion of the biologic material slurry produces a smooth layer or skin on an outer surface of the composition.

In certain embodiments, the method can include supporting the synthetic material substrate and at least the portion of the biologic material slurry during freeze drying such that the smooth layer or skin forms on an upper surface and an opposing lower surface of the composition. In certain embodiments, the method can include reorienting the synthetic material substrate and at least the portion of the biologic material slurry during freeze drying or between freeze drying processes such that the smooth layer or skin forms on an upper surface and an opposing lower surface of the composition.

In certain embodiments, the method can include freeze drying a first composition in a mold to form a first smooth layer or skin, removing the first composition from the mold and removing the first smooth layer or skin (e.g., in the form of a sheet or thin layer) from the first composition, flipping the first smooth layer or skin upside down and placing the first smooth layer or skin into a mold with the first smooth layer or skin facing a bottom, inner surface of the mold, pouring the biologic material slurry onto the first smooth layer or skin to cover the first smooth layer or skin with the biologic material slurry, positioning a second synthetic material substrate on the biologic material slurry, placing a second biologic material slurry to cover or coat at least a portion of a second synthetic material substrate such that the second biologic material slurry faces an open end of the mold, and freeze drying the second synthetic material substrate, the first smooth layer or skin, and the second biologic material slurry to form a second composition with a second smooth layer or skin on an outer surface of the second composition, the first smooth layer or skin attaching to the second composition during freeze drying resulting in the second composition including a first surface with the first smooth layer or skin and a second surface with the second smooth layer or skin. In certain embodiments, the first composition can include only the biologic material (i.e., not a combination of a biologic material with a synthetic material) to form the first smooth layer or skin to be used with the second composition. Thus, one synthetic material substrate can be used in forming the composition with the first and second smooth layers or skins. It should be understood that the first smooth layer or skin removed from the first composition includes an outer surface with the smooth layer or skin and an inner surface on an opposite side of the first smooth layer or skin. The second biologic material slurry between the second synthetic material substrate and the inner surface of the sheet of first smooth layer or skin promotes attachment of the inner surface of the sheet of first smooth layer or skin to the second synthetic material substrate. In addition, the second biologic material slurry increases the thickness of the second composition (both before and after compression). The resulting composition includes two surfaces (e.g., opposing surfaces), each with a smooth outer layer or skin.

According to certain embodiments, a composition for treatment is provided. The composition can include a synthetic material substrate and a biologic material attached to the synthetic material substrate. The biologic material can be in the form of a slurry freeze dried into a sponge and covering the synthetic material substrate. At least a portion of the biologic material can include a smooth layer or skin on an outer surface produced during freeze drying of the slurry.

According to certain embodiments, a method of treatment is provided. The method can include selecting an anatomic site and implanting in or on the anatomic site a composition as described above.

According to certain embodiments, a method of forming a composition for treatment is provided. The method can include providing a synthetic material substrate. The method can further include creating a biologic material slurry with the biologic material. The method can include incorporating at least a portion of the biologic material slurry into the synthetic material substrate to form a composition. Incorporating the biologic material slurry into the synthetic material substrate can include physically rubbing or otherwise mechanically moving the biologic material slurry into the synthetic material substrate. In certain embodiments, the method can include reducing a particle size of the biologic material to form a group of biologic material fragments.

Creating the biologic material slurry can include creating acid-swelled biologic material with at least a portion of the biologic material. The method can include contacting the biologic material with an acid and incubating the biologic material until swelling occurs. The acid can be at least one of acetic acid, ascorbic acid, boric acid, carbonic acid, citric acid, hydrochloric acid, lactic acid, tannic acid, phosphoric acid, and sulfuric acid. The method can include mixing the acid-swelled biologic material with non-swelled biologic material to form a biologic material slurry. Increasing a percentage by volume of the acid-swelled biologic material in the biologic material slurry can increase a stiffness of the resulting composition.

In certain embodiments, an antimicrobial compound can be incorporated into the composition. The antimicrobial compound can be at least one of chlorhexidine, silver (ionic, elemental, or salts), citric acid, triple antibiotic, tetracycline, other antibiotics, or combinations thereof. In certain embodiments, an anti-inflammatory compound can be incorporated into the composition.

In certain embodiments, the synthetic material substrate can be in the form of a three-dimensional form or construct. The synthetic material substrate can include at least one of a porous foam, a planar mesh, a monofilament woven material, a multifilament woven material, multi-leveled layers, multi-directional layers, or combinations thereof. A mechanical strength (tensile strength, burst strength, or suture retention strength) of the synthetic material substrate can be greater than a biomechanical strength of the biologic material. The synthetic material substrate can be biocompatible. In certain embodiments, the synthetic material substrate can be at least one of polypropylene, polytetrafluoroethylene, polyester, terephthalate, polyglycolide, poly-4-hydroxybutyrate, or combinations thereof. In certain embodiments, the synthetic material substrate can include one or more textured surfaces.

The biologic material can include a tissue matrix. In certain embodiments, the biologic material can include a collagen containing tissue matrix. In certain embodiments, the tissue matrix can include an acellular tissue matrix. In certain embodiments, the tissue matrix can include an acellular dermal matrix. In certain embodiments, the tissue matrix can include a porcine tissue matrix or a human tissue matrix.

In some cases, the biologic material slurry can be mechanically forced or processed (e.g., physically rubbed, mechanically moved, or otherwise mechanically processed) into the synthetic material substrate. In certain embodiments, physically rubbing or mechanically moving and compressing the biologic material slurry into the synthetic material substrate creates a coating of the biologic material slurry on an outer surface of the synthetic material substrate, thereby encasing at least a portion of the synthetic material substrate in the biologic material slurry.

The method can include pouring a portion of the biologic material slurry into a mold to cover a bottom of the mold with the biologic material slurry. The method can include positioning the synthetic material coated with, encased within, or embedded within the biologic material slurry into the mold on the biologic material slurry. The method can include pouring additional biologic material slurry over the synthetic material positioned in the mold to cover the synthetic material. The method can include drying, e.g., freeze drying, the composition to attach or embed the biologic material to the synthetic material (and/or cover, encase and/or coat the synthetic material with the biologic material).

According to certain embodiments, a composition for treatment is provided. The composition can include a synthetic material and a biologic material embedded to, attached to, coating, or covering the synthetic material. The biologic material can be in the form of a biologic material slurry. The biologic material slurry can be incorporated into the synthetic material by physically rubbing, mechanically moving, or otherwise mechanically processing the biologic material slurry into the synthetic material.

In certain embodiments, a particle size of the biologic material can be reduced to form a biologic material fragment for forming the biologic material slurry. In certain embodiments, processing of the biologic material can include cell removal and processing to remove antigenic components. In certain embodiments, the processing can be performed prior to mechanical processing of the biologic material to reduce the particle size of the biologic material. In certain embodiments, the processing can be performed after mechanical processing of the biologic material to reduce the particle size of the biologic material. In certain embodiments, the biologic material can be processed by a decellularization process.

In certain embodiments, at least a portion of the biologic material slurry can include acid-swelled biologic material. In certain embodiments, the composition can include an antimicrobial compound. In certain embodiments, the composition can include an anti-inflammatory compound.

In certain embodiments, the synthetic material can define a three-dimensional form or construct. In certain embodiments, the synthetic material can include at least one of a porous foam, a planar mesh, a multifilament woven material, multi-leveled layers, multi-directional layers, or combinations thereof. The biomechanical strength of the synthetic material can be greater than the biomechanical strength of the biologic material. The synthetic material can be biocompatible. In certain embodiments, the synthetic material can include at least one of polypropylene, polytetrafluoroethylene, polyester, terephthalate, or combinations thereof. In certain embodiments, the synthetic material can include one or more textured surfaces.

The biologic material can include a tissue matrix. In certain embodiments, the tissue matrix can include an acellular tissue matrix. In certain embodiments, the tissue matrix can include an acellular dermal matrix. In certain embodiments, the tissue matrix can include a porcine tissue matrix.

Physically rubbing, mechanically moving or otherwise mechanically processing the biologic material slurry into the synthetic material can force at least a portion of the biologic material slurry into the synthetic material. In certain embodiments, physically rubbing, massaging, mechanically moving, or otherwise mechanically processing the biologic material slurry into the synthetic material can create a coating of the biologic material slurry on an outer surface of the synthetic material, wherein the coating may be embedded within opening or porous portions in the synthetic material. The synthetic material and the biologic material slurry can be freeze dried and/or air dried to embed or attach the biologic material to the synthetic material (and/or cover or coat the synthetic material with the biologic material).

According to certain embodiments, a method of producing a composition or surgical material is provided. The method can include providing a synthetic material and providing a biologic material. The method can include creating a biologic material slurry with the biologic material. The method can include incorporating the biologic material slurry into and covering the surface of the synthetic material to form the composition. In particular, incorporating the biologic material slurry into and covering the surface of the synthetic material can include mechanically processing or forcing (e.g., physically rubbing, mechanically moving, or the like) the biologic material slurry into the synthetic material. Thus, the biologic material slurry can be mechanically forced into openings in the surface(s) of the synthetic material to substantially cover the outer surfaces of the synthetic material. The method can include at least partially covering a defect or implant site with the composition.

The composition can promote tissue ingrowth and regeneration of tissue surrounding the composition after implantation. Including between approximately 5% and approximately 35% by volume of acid-swelled biologic material slurry to form the composition can stabilize the composition. Physically rubbing, compressing, otherwise mechanically moving the biologic material slurry into the synthetic material can produce a strong attachment between the synthetic and biologic material. Suspending or reorienting the composition during freeze drying results in smooth layers or skin formed on one or more surfaces of the composition, providing a greater structural integrity to the composition.

DESCRIPTION OF THE DRAWINGS

FIG. 1 is a flow chart of an exemplary process of preparing a composition, according to certain embodiments;

DESCRIPTION OF CERTAIN EXEMPLARY EMBODIMENTS

Figure 2:
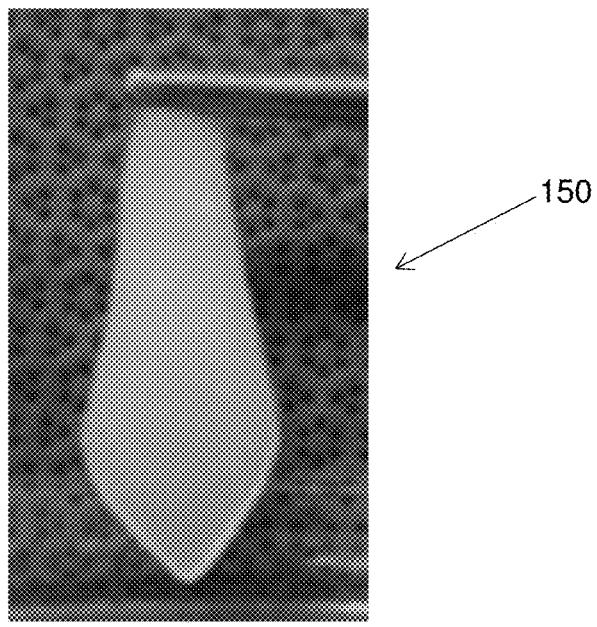
FIG. 2 is a front view of an exemplary composition including 0% by volume of acid-swelled biologic material as a percentage of the biologic material component, according to certain embodiments.
Figure 3:
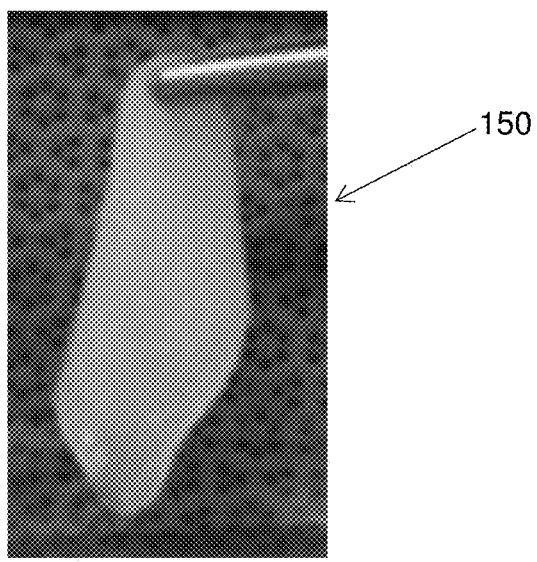
FIG. 3 is a front view of an exemplary composition including 5% by volume of acid-swelled biologic material as a percentage of the biologic material component, according to certain embodiments.
Figure 4:
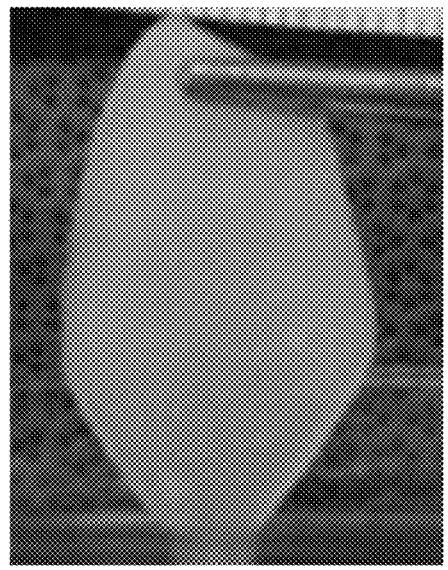
FIG. 4 is a front view of an exemplary composition including 10% by volume of acid-swelled biologic material as a percentage of the biologic material component, according to certain embodiments.
Figure 5:
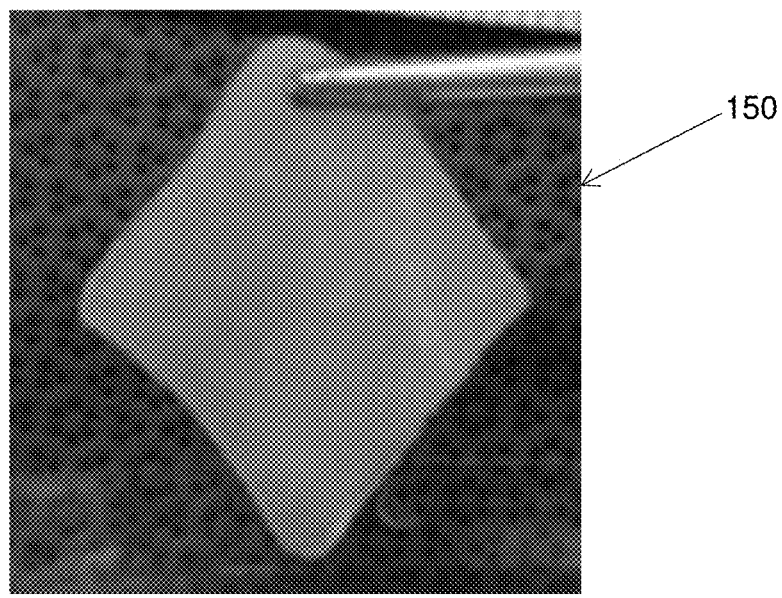
FIG. 5 is a front view of an exemplary composition including 25% by volume of acid-swelled biologic material as a percentage of the biologic material component, according to certain embodiments.
Figure 6:
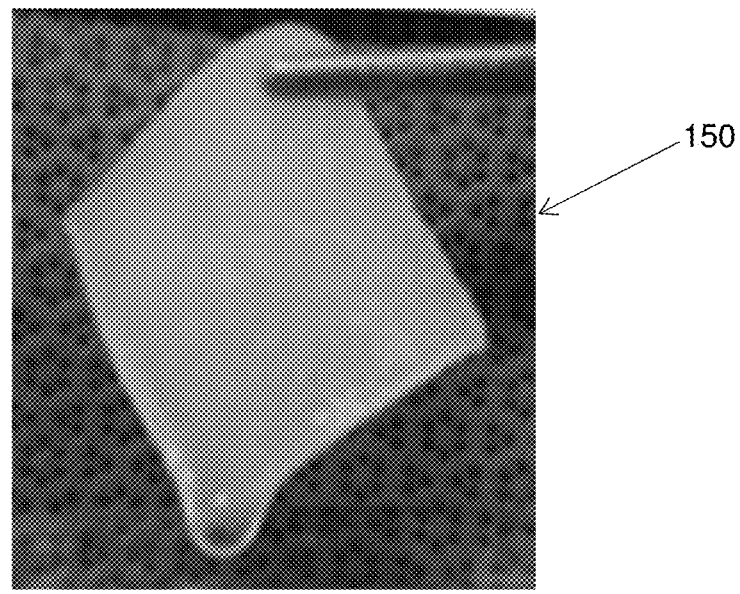
FIG. 6 is a front view of an exemplary composition including 50% by volume of acid-swelled biologic material as a percentage of the biologic material component, according to certain embodiments.
Figure 7:
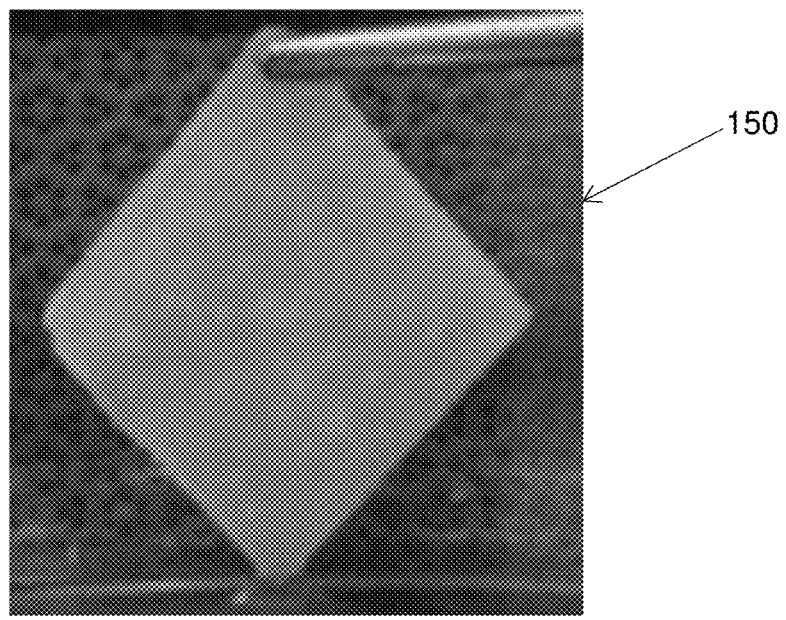
FIG. 7 is a front view of an exemplary composition including 100% by volume of acid-swelled biologic material as a percentage of the biologic material component, according to certain embodiments.
Figure 8:
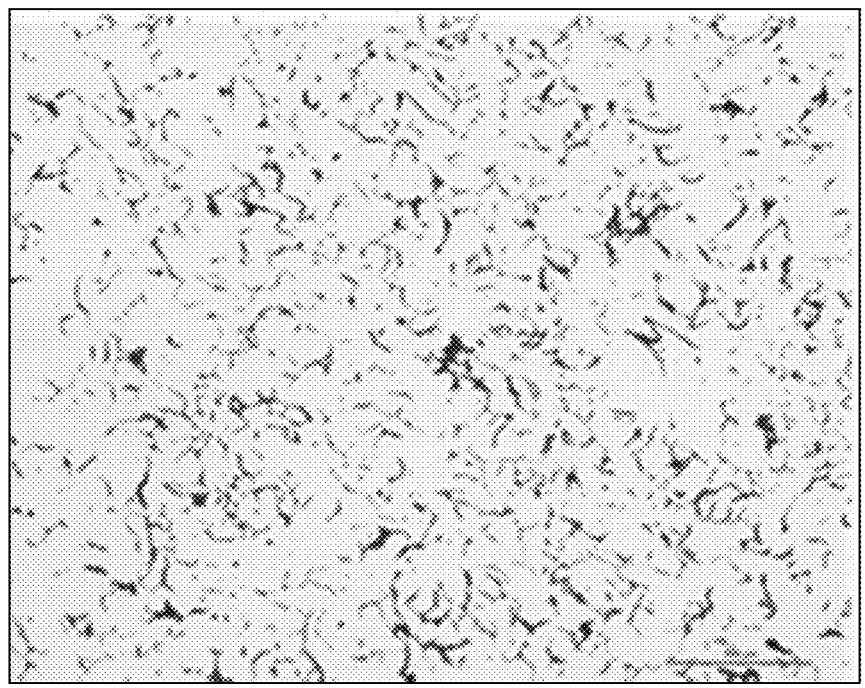
FIG. 8 is a magnified view of an exemplary composition including 0% by volume of acid-swelled biologic material as a percentage of the biologic material component with trichrome staining, according to certain embodiments.
Figure 9:
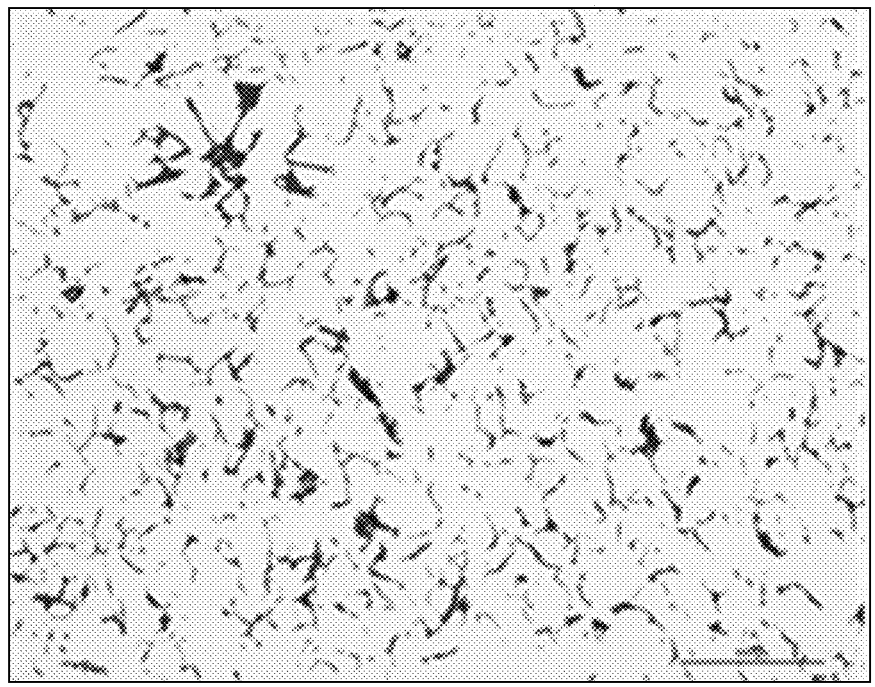
FIG. 9 is a magnified view of an exemplary composition including 5% by volume of acid-swelled biologic material as a percentage of the biologic material component with trichrome staining, according to certain embodiments.
Figure 10:
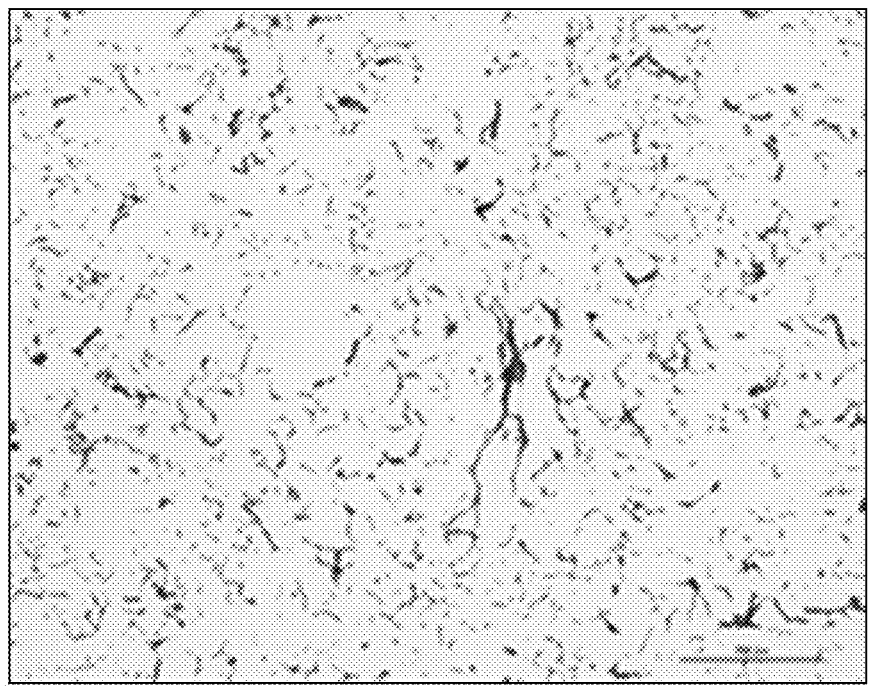
FIG. 10 is a magnified view of an exemplary composition including 10% by volume of acid-swelled biologic material as a percentage of the biologic material component with trichrome staining, according to certain embodiments.
Figure 11:
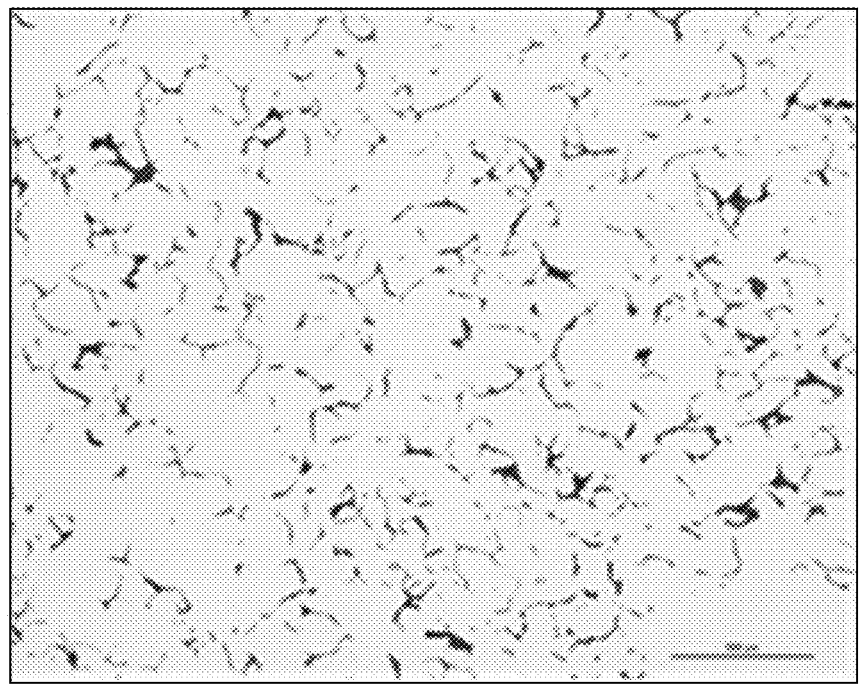
FIG. 11 is a magnified view of an exemplary composition including 25% by volume of acid-swelled biologic material as a percentage of the biologic material component with trichrome staining, according to certain embodiments.
Figure 12:
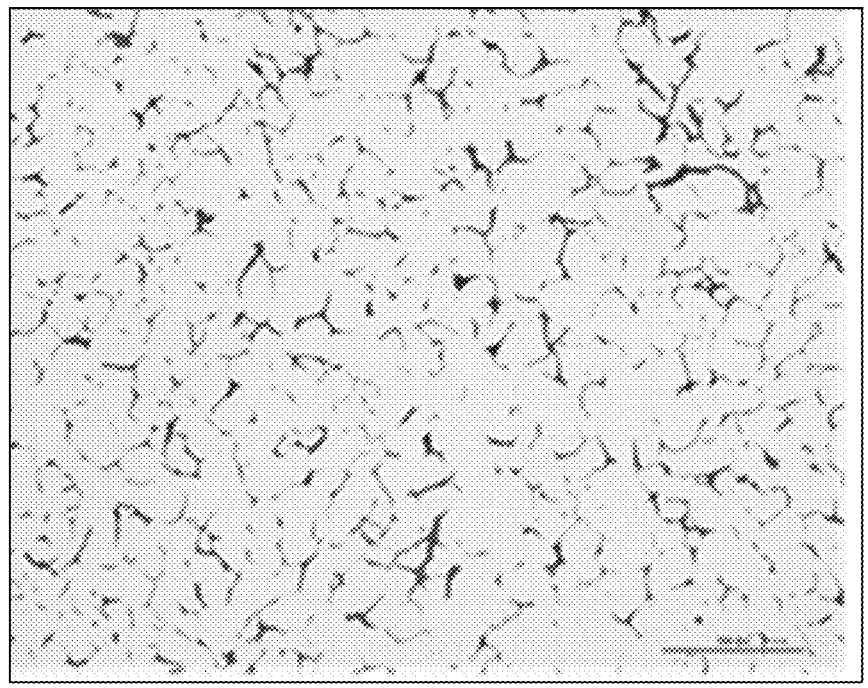
FIG. 12 is a magnified view of an exemplary composition including 50% by volume of acid-swelled biologic material as a percentage of the biologic material component with trichrome staining, according to certain embodiments.
Figure 13:
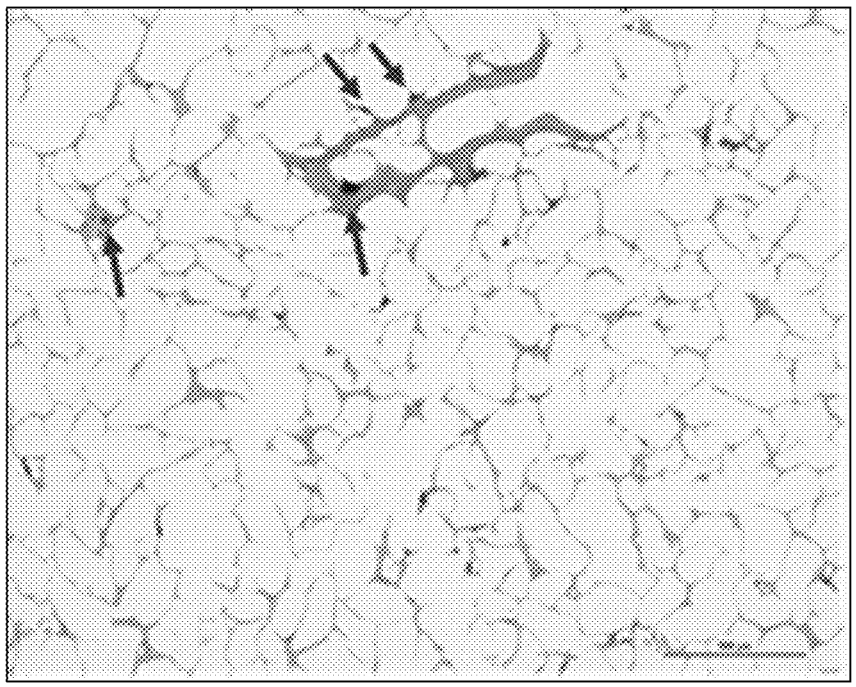
FIG. 13 is a magnified view of an exemplary composition including 100% by volume of acid-swelled biologic material as a percentage of the biologic material component with trichrome staining, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure is directed to exemplary compositions for treatment of structural defects, such as abdominal defects. The compositions include a combination of biologic and synthetic materials. In particular, the exemplary compositions include biologic materials attached to or embedding the synthetic material such that the composition can be manipulated during surgery without separation of the biologic and synthetic materials. The compositions can be folded or rolled to pass through a trocar or other opening for laparoscopic or other minimally invasive surgery. The attachment between the biologic and synthetic materials provides strength to the composition while allowing the composition to be flexed or otherwise manipulated during implantation. Furthermore, the synthetic material can provide a high level of tensile strength, burst strength, and/or suture retention strength, while the biologic material provides improved biologic responses, including a reduction in inflammation, a reduction in or prevention of scar or fibrotic tissue formation around the implant, and a reduction in or prevention of adhesion with surrounding viscera.

The hybrid composition allows the biologic material to function as a barrier to block the recognition by the host defense system, thereby reducing the foreign body response to the synthetic material. The biologic material can integrate with the host tissue and allows for vascularization, thereby reducing the possibility of infection. Further, the durability of the synthetic material provides mechanical advantages (e.g., strength and limited stretchability) for a treatment site, resulting in a durable repair of the host tissue.

Biologic Materials

Various human and animal tissues (e.g., biologic materials) can be used to produce products or compositions for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

In certain embodiments, these products or compositions can be completely or partially decellularized to yield acellular tissue matrices or extracellular tissue materials to be used for patients. For example, various tissues, such as skin, intestine, bone, cartilage, muscle (skeletal or otherwise), fascia, dermis nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

Tissue products can be selected to provide a variety of different biological and mechanical properties. For example, an acellular tissue matrix or other tissue product can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices, respectively. Alternatively, other suitable acellular tissue matrices are available, as described further below. For example, a number of biological scaffold materials are described by Badylak et al. Badylak et al., "Extracellular Matrix as a Biological Scaffold Material: Structure and Function," *Acta Biomaterialia* (2008), doi:10.1016/j.actbio.2008.09.013. In certain embodiments, the compositions discussed herein can be formed from or can include a tissue product, a synthetic material, or both.

The term "acellular tissue matrix," (e.g., ATM) as used herein, refers generally to any tissue matrix that is substantially free of cells and/or cellular components. Skin, parts of skin (e.g., dermis), and other tissues such as blood vessels, heart valves, fascia, cartilage, bone, fascia, muscle (skeletal or non-skeletal) and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components.

In general, the steps involved in the production of an acellular tissue matrix include harvesting the tissue from a donor (e.g., a human cadaver or animal source) and cell removal under conditions that preserve biological and structural function. The ATM can be produced from any collagen-containing soft tissue and musculo-skeletal tissue (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, in certain embodiments, the tissues in which the above ATMs are placed include any tissue that can be remodeled by invading or infiltrating cells. Relevant tissues include, without limitation, skeletal tissues such as bone, cartilage, ligaments, fascia, and tendon. Other tissues in which any of the above allografts can be placed include, without limitation, skin, gingiva, dura, myocardium, vascular tissue, neural tissue, striated muscle, smooth muscle, bladder wall, ureter tissue, intestine, and urethra tissue.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

One exemplary method for making (or preparing) an ATM can include the steps of: optionally providing a tissue sample from a mammal; removing all, or substantially all, of the cells from the tissue sample resulting in a decellularized tissue; and contacting the decellularized tissue with a DNA nuclease that removes all, or substantially all, of the DNA from the decellularized tissue, thereby resulting in an ATM.

Decellularization of a tissue can be accomplished using a number of chemical or enzymatic treatments known in the art and described in, e.g., U.S. Pat. No. 5,336,616 (the disclosure of which is incorporated by reference in its entirety). For example, cells can be removed from a tissue by incubating the tissue in a processing solution containing certain salts (e.g., high concentrations of salts), detergents (e.g., mild or strong detergents), enzymes, or combinations of any of the foregoing. Strong detergents include, e.g., ionic detergents such as, but not limited to: sodium dodecyl sulfate, sodium deoxycholate, and 3-[(3-chloramidopropyl)-dimethylammino]-1-propane-sulfonate. Mild detergents include, e.g., polyoxyethylene (20) sorbitan mono-oleate and polyoxyethylene (80) sorbitan mono-oleate (TWEEN 20 and 80), saponin, digitonin, TRITON X-100™, CHAPS, and NONIDET-40 (NP40). The use of the detergent TRITON X-100™, a trademarked product of Rohm and Haas Company of Philadelphia, Pa., has been demonstrated to remove cellular membranes, as detailed in U.S. Pat. No. 4,801,299, the entire contents of which are incorporated by reference in their entirety. Alternatively, decellularization can be accomplished using a variety of lysogenic enzymes including, but not limited to, dispase II, trypsin, and thermolysin.

A tissue can be treated once or more than once (e.g., two, three, four, five, six, seven, eight, nine, or 10 or more times) with a processing solution. A tissue can be treated more than one time with the same processing solution or can be treated with several different processing solutions in series. For example, a tissue can be treated with one processing solution multiple times or the tissue can be treated with a first processing solution and subsequently with a second processing solution.

As the processing solution can contain chemicals or agents that would be irritating or inflammatory when administered to a mammalian subject, washing can be performed to substantially remove the processing solution from the tissue. In some embodiments, a tissue can be washed one or more (e.g., two, three, four, five, six, or more than seven) times following treatment with a processing solution or the tissue can be washed one or more times between processing solution treatments. For example, a tissue can be treated with a first processing solution and then washed three times before treatment with a second processing solution. Alternatively, rather than or in addition to, components of the processing solution may be neutralized by inhibitors, e.g., dispase II by ethylenediaminetetraacetic acid (EDTA) or trypsin by serum.

Methods for determining the extent of decellularization are known in the art and include, e.g., cell-counting/trypan blue exclusion assays (on any cells collected from a treated tissue) or various microscopy methods such as direct immunostaining of a decellularized tissue section using antibodies that bind to specific cell markers (e.g., markers of the cell nucleus, mitochondria, or cell cytoplasm). Such methods are described in, e.g., Ramos-Vara, J A (2005) *Vet Pathol* 42: 405-426 and Hayat (2002) *Microscopy, Immunohistochemistry, and Antigen Retrieval Methods: For Light and Electron Microscopy*, 1$^{st}$ Ed. Springer, the disclosures of each of which are incorporated by reference in their entirety.

Synthetic Materials

The synthetic materials discussed herein can be fabricated from a variety of different biocompatible and/or resorbable materials. For example, the synthetic materials can include polypropylene (PP), polytetrafluoroethylene (PTFE), polyester (i.e., polyethylene terephthalate (PET)), polyglycolide (PGA), poly-4-hydroxybutyrate (P4HB), or combinations thereof. In certain embodiments, the synthetic material can be in the form of a mesh substrate, e.g., a multifilament woven material, a monofilament woven material, or combinations thereof. In certain embodiments, the synthetic material can be in the form of a porous foam, multi-leveled and/or multi-directional layers, or combinations thereof. In certain embodiments, the synthetic material can be printed with a three-dimensional printer to produce a three-dimensional scaffold.

In certain embodiments, the synthetic material can be fabricated from a non-absorbable material, an absorbable material, or a material that is a combination of both non-absorbable and absorbable materials. "Absorbable material" can be defined herein as any material that can be degraded in the body of a mammalian recipient by endogenous enzymatic or cellular processes. Depending upon the particular composition of the material, the degradation products can be recycled via normal metabolic pathways or excreted through one or more organ systems. A "non-absorbable material" can be defined herein as any material that cannot be degraded in the body of a mammalian recipient by endogenous enzymatic or cellular processes.

In certain embodiments, the synthetic material can provide the ability to produce various textures (e.g., loops and hooks, rough textures, or combinations thereof) to assist in attachment or handling. For example, the textured surface of the synthetic material can assist with attachment of the biologic material to the synthetic material.

The synthetic material can be formed in various colors to act as a visual aid during final implantation or for identification during subsequent procedures or if explant is ever desired. For example, the color of the synthetic material can differ from the biologic material and the surrounding tissue to better accommodate the implant site cavity and provide ease of suture location during the surgical procedure.

The synthetic material can be used to provide a controlled reinforcement (e.g., a rebar), strength, thickness, rate of biologic degradation, or combinations thereof, in varying regions of the composition. For example, the synthetic material can be positioned in areas of the composition that will require the most strength to provide support to the defect site.

In certain embodiments, cohesion can be provided during layering of the biologic and synthetic materials or components. In certain embodiments, different layers of synthetic material can be at periodic angles relative to one another (e.g., similar to manufacturing of plywood) to produce a multidirectional strength within the composition. In particular, the synthetic material can extend in different directions and/or at different angles to provide greater strength and support to the composition.

In certain embodiments, rather than a synthetic material or substrate, a biologic substrate material (e.g., a biologic mesh) can be used. For example, the biologic substrate material can be fabricated from any biocompatible material (e.g., silk, a cellulose matrix, or combinations thereof) suitable for coating and/or embedding with biologic material. A hybrid composition formed from two biologic materials can thereby be formed.

Composition Preparation

The compositions discussed herein include a combination of biologic materials and synthetic materials. In particular, the compositions generally include a sheet of synthetic material covered with and attached to or embedded into biologic materials. The compositions can be used to treat defective or damaged tissue, or to reinforce existing tissues. The compositions provide beneficial properties provided of both the biologic and synthetic materials, and further provide improvements in ease of suturability, strength of suture points, a wide array of manufacturability (e.g., shape, size, or thickness), decrease in infection due to the biologic material, incorporation of anti-microbial agents, layered technology to control a rate of degradation, elution of enzymes and anti-microbial agents, and a reduction in inflammation. The compositions also provide for a strong attachment between or embedding of the biologic and synthetic materials. In particular, the compositions can be flexible while maintaining the attachment between the biologic and synthetic materials, such that the compositions can be manipulated easily during surgery without separation of the components. For example, the compositions can be rolled and passed through a trocar into an implantation site without separation of the synthetic material from the biologic material.

The compositions can be in the form of bio-synthetic hybrid surgical three-dimensional scaffolds for tissue treatment, attachment, reinforcement or reconstruction that minimizes complications and promotes tissue ingrowth, leading to overall improved surgical outcomes. The inherent biomechanical strength of the synthetic material can be much higher than that of biologic material alone. The composition can be manufactured to any shape and/or size, while maintaining the biological advantages typically associated with biologic materials (e.g., rapid revascularization, cell repopulation, white cell migration, or combinations thereof). Therefore, the exemplary compositions lend themselves to a wide array of surgical applications in a variety of sites including abdominal surgery, urologic applications, thoracic surgery, orthopedic surgery, breast reconstruction or augmentation, or other surgical applications in which composite materials may be of used. The devices can be used in minimally invasive or open surgeries.

With reference to FIG. 1, one embodiment of a process of preparing a composition is provided. The processing of the biologic material described herein can be selected to accomplish desired cell or antigen removal, while ensuring that the biologic material retains the ability to support tissue regeneration, rapid revascularization and cell repopulation, and does not induce a significant inflammatory response when implanted. It should be understood that one or more steps of the exemplary process can be omitted, and the order of some steps may be changed.

At step 100 of FIG. 1, the harvested biologic material can be pre-processed. For example, the biologic material or component can be harvested from a tissue site such as the dermis, fatty tissue, peritoneum, the intestines, and can be pre-processed in preparation for preparing the composition. Such preprocessing may include removal of unwanted tissues or related structures and storage prior to use.

At step 102, the particle size of the biologic material can be reduced. For example, the originally harvested biologic material can be reduced in size to produce a group of biologic material fragments. In certain embodiments, a tissue or meat chopper/grinder can be used to reduce the particle size of the biologic material. The biologic material can be reduced in particle size such that the group of biologic material fragments are substantially similar in size and/or configuration or within a preselected size range. In certain embodiments, the size and/or configuration of the biologic material fragments can be regulated based on a selection of the grinder, the size of the rotor, or the size of the stator used for grinding; alternatively, the tissue can be filtered or selected to produce desired size distributions. In some embodiments, a meat chopper/grinder, a mill, or other similar mechanical processing device can be used to reduce the particle size of the biologic material in a liquid at room temperature.

Figure 31:
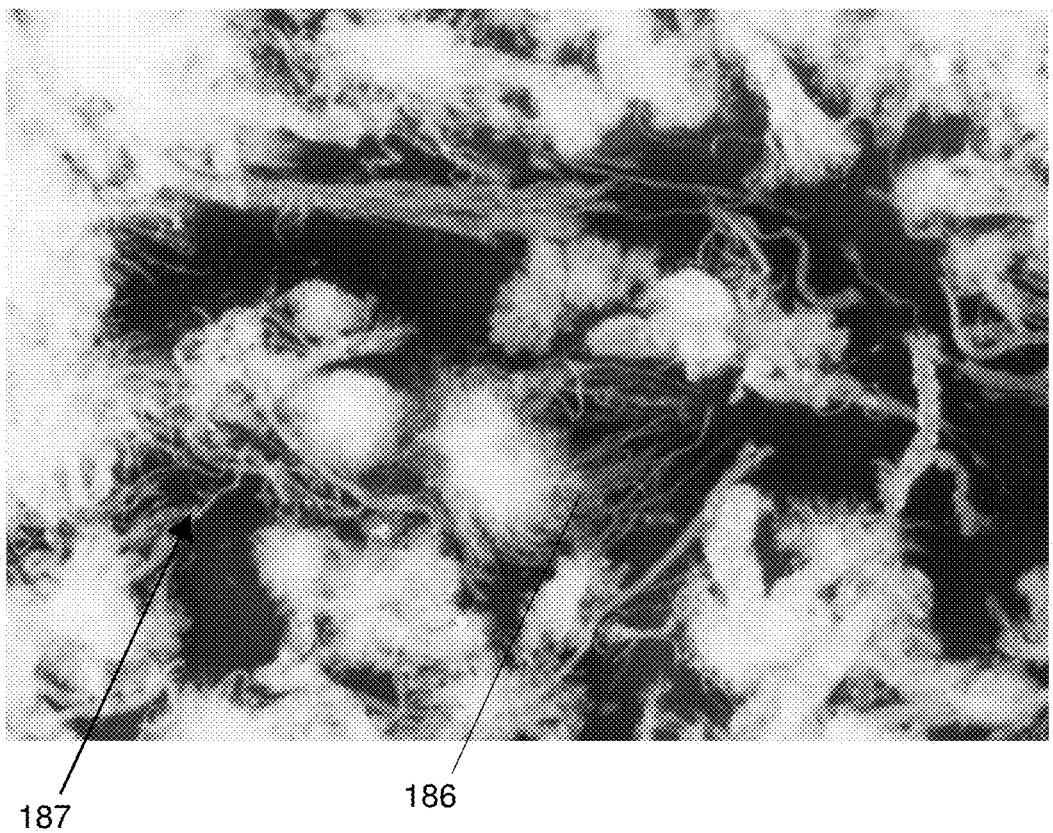
FIG. 31 is a microscopy image of reduced size biologic material including tendrils or frayed ends, and interlocking of the tendrils or frayed ends, according to certain embodiments.

In certain embodiments, the biologic material can be reduced in size such that the biologic material fragments or fibers have frayed ends. In certain embodiments, a predetermined setting of the rotor and stator of the grinder can be used to produce the desired tendrils or frayed ends of the biologic material fragments. FIG. 31 is a microscopy image of reduced size biologic materials at approximate 30× magnification. The fragments of the biologic material include tendrils or frayed ends 186. FIG. 31 illustrates an example of the tangling or interlocking 187 of the tendrils or frayed ends 186 of the fragments. As an example, the fragments with frayed ends 186 can be formed by shear during the chopping and/or grinding process. The frayed ends 186 can promote interlocking 187 between the biologic material fragments during formation of the composition, resulting in a strong overall structure of the composition.

At step 104, the biologic material fragments can be further processed. In certain embodiments, the biologic material fragments can be processed to remove cells and/or antigenic materials such as DNA, antigenic epitopes (e.g., alpha-galactose residues). In certain embodiments, the processing can be performed prior to reducing the size of the biologic material by mechanical processing. Alternatively, tissue processing (such as cell removal) can be performed before fragment formation or simultaneously therewith. In certain embodiments, the frayed ends (or a portion of the frayed ends) of the biologic material fragments can be coated with an anti-inflammatory compound or mixed with such compounds to prevent or reduce inflammation due to implantation or the surgical procedure.

The order of the initial processing and size reduction steps may be varied. In certain embodiments, the biologic material can be pre-processed (e.g., as described in step 100), a size reduction of the biologic material can be performed after pre-processing (e.g., as described in step 102), and further processing steps can be taken after the size reduction of the biologic material (e.g., as described in step 104). In certain embodiments, the biologic material can be pre-processed, further processing steps can be taken after pre-processing, and size reduction of the biologic material can be performed after both the pre-processing and processing steps. In certain embodiments, size reduction of the biologic material can initially be performed, pre-processing of the biologic material can be performed after the size reduction, and further processing can be performed after the pre-processing step.

At step 106, a slurry can be prepared with the biologic material fragments. In certain embodiments, due to the size reduction of the biologic material, the fragments in a solution can form the disclosed slurry. In certain embodiments, after step 104, the biologic material fragments can be centrifuged after each step during processing in order to pellet the tissue and remove the old solution. After the next solution is added, the pellet can be resuspended and allowed optionally allowed to incubate or wash in the new solution. The new solution can be removed from the slurry by centrifuging. This process can be repeated during each processing step. The process of preparing the slurry can include an acid-swelling procedure of at least a portion (e.g., five percent) of the biologic material fragments. The acid-swelling procedure can include the steps of selecting a portion (e.g., 5%) of the biologic material slurry (based on a volume of the biologic material slurry), centrifuging the selected slurry to pellet the biologic material, removing the old solution, resuspending the pellet in a volume of acid solution that is equal to the volume of old solution removed in the previous step, incubating the slurry (e.g., for 1-8 hours at approximately 33-40° C.), and combining the acid-swelled biologic material with the rest of the non-acid-swelled biologic material slurry.

In certain embodiments, the concentration of the acid solution used for the acid-swelling procedure can affect the final characteristics of the composition. For example, a certain concentration of the acid solution can result in a slurry having multiple visible dermal fibers, while a different concentration of the acid solution can result in a slurry having a more liquid consistency with fewer visible dermal fibers. The resulting different concentrations can affect attachment of the biologic material to the synthetic material. In particular, the amount of acid-swelled biologic tissue by volume and the concentration of the acid solution can affect the structural stability of the resulting composition. In certain embodiments, formation of the biologic material slurry can include between, e.g., 5-25%, 5-20%, 5-15%, or 5-10%, of acid-swelled biologic tissue by volume, resulting in strong structural stability of the composition.

In certain embodiments, the biologic material slurry can include, e.g., 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-95%, 0-90%, 15-85%, 20-80%, 25-75%, 30-70%, 35-65%, 40-60%, 45-55%, 5-35%, 5-30%, 5-25%, 5-20%, 5-15%, 5-10%, 5%, 10%, 25%, 50%, or 100%, of acid-swelled biologic material by volume, with the remaining slurry including non-acid-swelled material. In preferred embodiments, the biologic material slurry can include, e.g., 5-35%, 5-30%, 5-25%, 5-20%, 5-15%, or 5-10%, of acid-swelled biologic material by volume, with the remaining slurry including non-acid-swelled material. Too much acid-swelled material (e.g., above approximately 35% by volume) can result in higher levels of inflammation and biologic degradation upon implantation. Conversely, an insufficient amount of acid-swelled material (e.g., below approximately 5% by volume) can result in a lack of structural stability of the composition. Therefore, the amount of acid-swelled biologic material can be controlled to reduce inflammation and to provide sufficient structural stability to the composition. The tolerance for inflammation and need for structural stability may vary based on the intended use.

The biologic material fragments can be washed one or more times and centrifuged to remove excess water or buffer. The pellet of biologic material can be resuspended in citric acid and incubated at approximately 37 C for approximately four hours until swelling occurs. In certain embodiments, the pH of the acid in which the biologic material is resuspended can be in the range of approximately 1-6, approximately 1-4, approximately 1.8-2.2, or about 2. The volume of acid used can be substantially equal to the volume of solution removed after centrifugation in order to maintain the solid percentage the same in the biologic material.

After acid swelling, the swelled biologic material can be mixed with non-swelled biologic material to form a slurry containing a specific percentage of swelled biologic material. As an example, a slurry can include dermal acellular tissue fragments resuspended in a liquid, and varying the percentage of swelled biologic material in the slurry affects the properties of the final composition. For example, increasing the percentage by volume of acid-swelled biologic material in a slurry can increase the stiffness of the resulting composition. In certain embodiments, a 100 percent acid-swelled slurry can be formed. In such embodiments, no dilution with non-swelled biologic material is made.

In certain embodiments, the biologic material can undergo an additional processing step(s). The processing of the biologic material can be selected to accomplish desired cell or antigen removal, while ensuring that the biologic material retains the ability to support tissue regeneration, rapid revascularization, cell repopulation, white cell migration, or combinations thereof, and does not induce a significant inflammatory response when implanted. The processing of the biologic material can be performed at one or more stages of the process described herein.

After the slurry of acid-swelled and non-swelled biologic material has been formed, the slurry can be placed in an appropriate buffer. For example, a suitable buffer can be sodium citrate buffer, PBS, or other buffers. In certain embodiments, the biologic material slurry can be at approximately three percent or seven percent by volume of solid biologic material. In certain embodiments, resuspending the slurry in the sodium citrate buffer can be performed prior to acid swelling.

At step 108, the biologic material slurry can be incorporated into a synthetic material to cover the outer surfaces of the synthetic material. In particular, the biologic material slurry can be mechanically forced, rubbed, or processed such that at least some of the biologic material is forced into openings in the outer surface of the synthetic material, thereby forming a film of biologic material on the outer surfaces of the synthetic material.

In certain embodiments, antimicrobial compounds (e.g., chlorhexidine, silver, citric acid, triple antibiotic, tetracycline, or combinations thereof) and/or anti-inflammatory compounds (e.g., for reduction of inflammation and/or anti-scarring), fibronectin, or combinations thereof) can be incorporated into the biologic material slurry and/or the synthetic material. In certain embodiments, the synthetic material can be in the form of a three-dimensional construct (e.g., a porous foam, a mesh, multi-leveled and/or multi-directional layers, or combinations thereof) that provides a three-dimensional scaffold for the biologic material. The synthetic material or component provides strength and sutureability to the composition, while the biologic material can mask the synthetic material to promote tissue ingrowth, reduce inflammation and/or scar formation, and minimize complications.

In certain embodiments, the biologic material slurry can be incorporated into the synthetic material by mechanically forcing or processing (e.g., physically rubbing, otherwise mechanically moving, or the like) at least a portion of the biologic material slurry into the synthetic material. Mechanically forcing or processing the biologic material slurry into the synthetic material can create a stronger attachment or engagement between the biologic and synthetic material, thereby preventing separation between the materials during use. Mechanically forcing or processing the biologic material slurry into the synthetic material forces portions of the biologic material into openings in the outer surface of the synthetic material and creates a thin coating of the biologic material on the outer surfaces of the synthetic material.

A portion of the biologic material slurry can be poured into a mold such that the bottom of the mold is covered by slurry. As discussed herein, the mold can be any structure or container used for shaping the resulting composition after the drying process. In certain embodiments, the mold can define a substantially rectangular, circular, oval, square, polygon, or curvilinear configuration. The coated or embedded synthetic material can be positioned within the mold on top of the slurry, and additional biologic material slurry can be poured over the synthetic material such that the slurry covers the synthetic material. It should be understood that the amount of slurry poured onto the bottom of the mold and over the synthetic material can be selected based on the desired thickness of the final composition.

At step 110, the coated synthetic material and the biologic material slurry can be dried, for example, by freeze drying. During the freeze drying process, the biologic material coating covering the outer surfaces of the synthetic material allows for a stronger attachment or engagement between the biologic material slurry surrounding the synthetic material in the mold and the synthetic material. In particular, the biologic material forced or compressed into the synthetic material and forming the coating provides a surface against which the biologic material slurry can attach. Further, the biologic material forced or compressed into the synthetic material creates a stronger attachment or engagement between the biologic material and the synthetic material during the freeze drying process due to interlocking of the biologic material around the synthetic material. The freeze drying process can be performed under conditions that maintain the desired biological and structural properties associated with the biologic and synthetic materials.

Figure 34:
FIG. 34 is a microscopy image of a composition including a synthetic material coated with a biologic material without a skin layer, according to certain embodiments.
Figure 35:
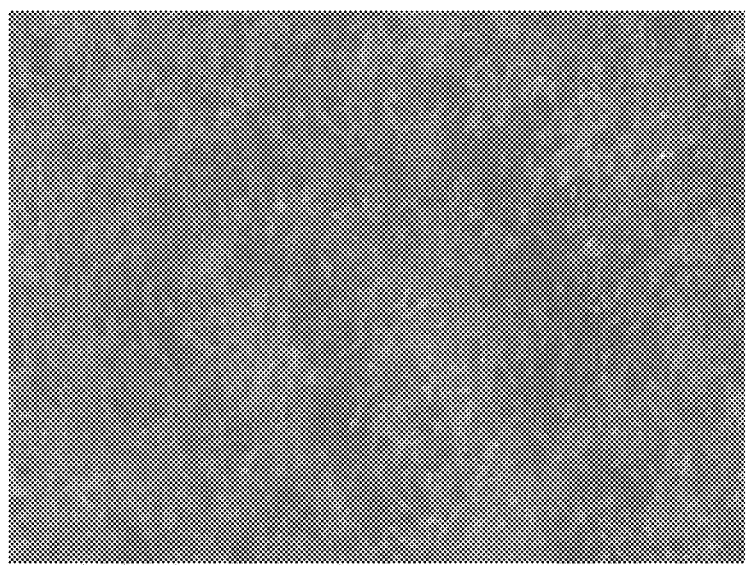
FIG. 35 is a microscopy image of a composition including a synthetic material coated with a biologic material with a skin layer, according to certain embodiments.

In certain embodiments, when the biologic material slurry and the synthetic material are positioned in the mold for freeze drying, one side of the composition is positioned against an inner surface of the mold, while the opposing side of the composition is exposed to the air (e.g., vacuum air). During the freeze drying process, collagen fibrils gradually form through each layer of the composition and latch on to adjacent material to create an attachment. When the collagen fibrils reach the uppermost and exposed layer of the composition, since there is no additional material to attach to, the collagen fibrils form a substantially smooth and flat layer, surface or skin. In general, the lowermost and side surfaces positioned within the mold form the collagen fibril bonds, but result in a rougher surface than the smooth layer formed on the uppermost and exposed layer. Unlike rough surfaces that create more friction and can flake off during use, the smooth layer reduces or prevents flaking of the composition due to reduced friction and strong attachment. As an example, FIG. 34 shows a microscopy image of a hybrid sponge without a smooth surface or skin layer, and FIG. 35 shows a microscopy image of a hybrid sponge with a smooth surface or skin layer.

In certain embodiments, a smooth skin layer can be formed on or added to the composition during the freeze drying process. In certain embodiments, rather than using a mold structure that encloses all of the surfaces except for the upper surface, the composition can be freeze dried in a mold structure that provides space around the sides of the composition (e.g., exposes multiple sides of the sponge or composition). Thus, only the bottom surface is positioned against the mold and the remaining surfaces can be exposed to air such that smooth surfaces or skin can form on most of the outer surfaces of the composition. In certain embodiments, rather than using a mold that encloses all of the surfaces except for the upper surface, the composition can be freeze dried on a substantially planar support structure that allows for the top and sides of the composition to be exposed to the air. Smooth surfaces or skin can thereby form on most of the outer surfaces of the composition.

In certain embodiments, after the smooth surfaces have formed on the top and sides of the composition, the composition can be suspended or repositioned to expose the bottom surface to air such that a smooth surface or skin can form on the bottom surface. Thus, smooth surfaces or skin can form on all of the surfaces of the composition. In certain embodiments, the orientation of the composition can be varied one or more times during the freeze drying process such that smooth surfaces or skin form on all of the surfaces of the composition. In certain embodiments, only one side of the composition can be coated with the biologic material slurry for freeze drying and, once the smooth surface or layer has formed, the composition can be flipped and the opposing side can be coated with the biologic material slurry for freeze drying, thereby achieving smooth surfaces or skin on both sides of the biologic material. In certain embodiments, the composition can be positioned on one of the side surfaces during the freeze drying process such that the top and bottom surfaces of the composition form the smooth surfaces or skin. In certain embodiments, a support structure can suspend or hold the composition during the freeze drying process in a configuration that exposes all sides (or at least the top and bottom sides) of the composition to allow the exposed sides to form the smooth surfaces or skin. The low friction surfaces results in a structurally stronger composition with reduces or no flaking of the material.

In certain embodiments, rather than or in addition to using a drying process that exposes multiple sides of the composition, a skin layer from one uncompressed sponge can be removed and repositioned such that the skin side is in contact with the inside bottom surface of the mold (e.g., not exposed to the atmosphere), biologic material slurry is poured over the first skin within the mold, and a second composition (including a synthetic material coated with the biologic material slurry) is positioned over the biologic material slurry such that the biologic material slurry coating the synthetic material is exposed at the opening of the mold. Freeze drying is performed again. The side of the second composition exposed to the atmosphere forms the skin layer while the previously placed skin layer maintains its composition and attaches to the second composition via the biologic material slurry, thereby forming a composition with skin layers on opposing sides.

Figure 36:
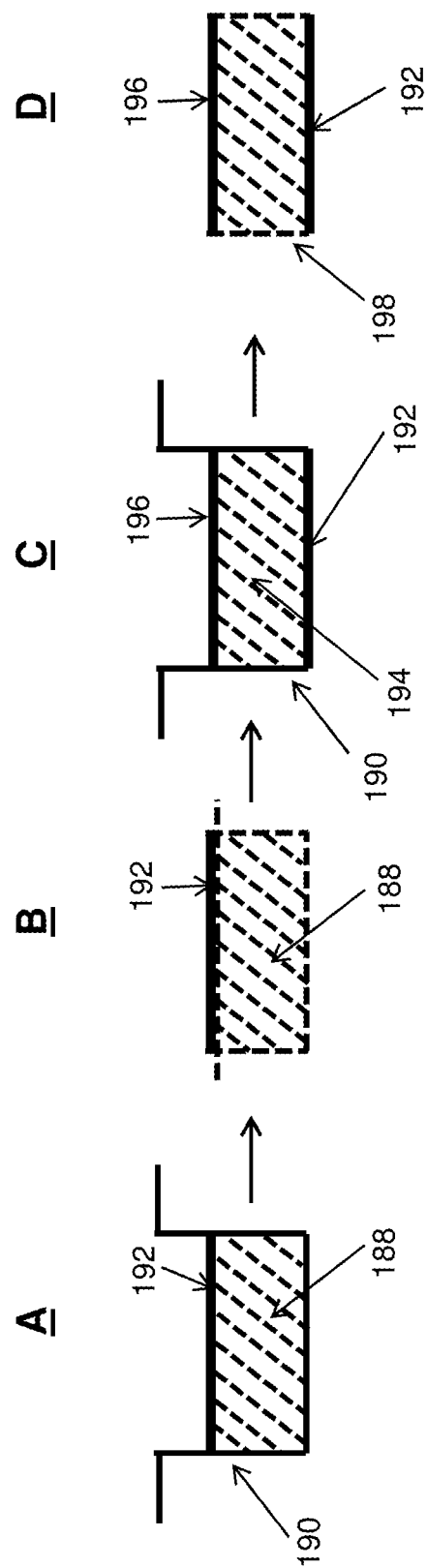
FIG. 36 is a diagrammatic view of a process for forming a skin layer on both sides of a composition including a synthetic material coated with a biologic material, according to certain embodiments.

FIG. 36 shows a diagrammatic view of the process for forming the smooth surface or skin layer on a composition (e.g., a hybrid sponge). Initially, at step A, a first hybrid composition 188 is formed by freeze drying the composition 188 in a mold 190. After freeze drying, the first hybrid composition 188 includes a first skin layer 192 (e.g., a top layer of the first hybrid sponge 188) formed on the surface of the composition 188 exposed through the top opening of the mold 190. In certain embodiments, the first hybrid composition 188 can be formed from both a biologic material and a synthetic material, and the first skin layer 192 can be removed while discarding the remaining portions of the composition 188. In certain embodiments, the composition 188 can be formed only from the biologic material without the synthetic material. Thus, after removal of the first skin layer 192 from the composition 188, only a portion of the biologic material can be discarded without necessitating discarding of the synthetic material, resulting in a more cost-effective process.

At step B, the first hybrid composition 188 can be removed from the mold 190 and the first skin layer 192 is removed (e.g., sliced) from the first hybrid composition 188

(e.g., in the form of a sheet). After removing the first skin layer 192 from the first hybrid composition 188, the first skin layer 192 includes an outer surface with the smooth surface and an inner surface that originally faced the inside of the first hybrid composition 188. At step C, the first skin layer 192 is flipped upside down and placed within a mold 190 such that the smooth surface of the first skin layer 192 faces the inside surface of the bottom of the mold 190. Biologic material slurry is poured over the inner surface of the first skin layer 192. A synthetic material 194 coated with biologic material is positioned over the biologic material slurry on the first skin layer 192, and additional biologic material slurry is poured on top of the synthetic material 194. The synthetic material 194, the biologic material slurry, and the first skin layer 192 can be freeze dried to form the final hybrid composition 198. The biologic material slurry within the mold 190 promotes attachment of the inner surface of the first skin layer 192 to the synthetic material 194. In addition, the biologic material slurry increases the thickness of the final hybrid composition 198 (both before and after compression).

The surface of the final hybrid composition 198 exposed at the opening of the mold 190 forms a second skin layer 196. At step D, the hybrid composition 198 can be removed from the mold 190. The hybrid composition 198 therefore includes one surface with the first skin layer 192 and an opposing surface with the second skin layer 196. It should be understood that the skin layers can be formed on different surfaces of the hybrid composition and do not necessarily need to be disposed on opposing surfaces of the hybrid composition. In addition, the process can be repeated to produce several skin layers that can be used to line the inside surfaces of the mold, thereby resulting in a hybrid composition that includes multiple sides with skin layers.

At step 112, the composition can be stabilized by additional steps to form a stable three-dimensional scaffold matrix. In certain embodiments, additional stabilization can be performed to maintain the structural integrity of the composition when exposed to fluids. For example, suitable stabilization processes can include various cross-linking or other processes to produce a 3-D shape. In certain embodiments, during use, the composition can be manipulated (e.g., rolled) to introduce the composition into an implant location, and the composition can further be rehydrated to expand into the original or natural configuration.

In certain embodiments, at step 114, in addition to or alternatively to mechanically forcing or processing the biologic material slurry into the synthetic material, a compression step can be performed to incorporate the biologic material slurry with the synthetic material and/or to increase the density of the biologic material embedding or coating the synthetic material. Although shown in FIG. 1 as occurring after step 112, it should be understood that step 114 can occur at any stage of the process. The compression step can generally be performed on a hydrated composition or sponge (e.g., the composition can be hydrated after the freeze drying step, or the composition can be stabilized in carbodiimide). In certain embodiments, the compression step can be performed on a freeze-dried composition. In particular, a coating of the biologic material slurry can be placed on one or more sides of the synthetic material. Next, the composition can be freeze dried. After freeze drying, the composition can be compressed on both sides at a predetermined pressure. In certain embodiments, a non-compressed sponge or composition can be hydrated and a predetermined load can be placed on the hydrated non-compressed sponge or composition for a specific amount of time (e.g., approximately two minutes). In certain embodiments, the sponge or composition can be placed back into a freeze dryer to dry again. In certain embodiments, rather than or in addition to freeze drying, the sponge or composition can be air dried. In particular, after the initial freeze drying procedure in step 110 that forms the sponge-like or porous structure, drying of the composition can be performed by either freeze drying, air drying, or both.

Figure 32:
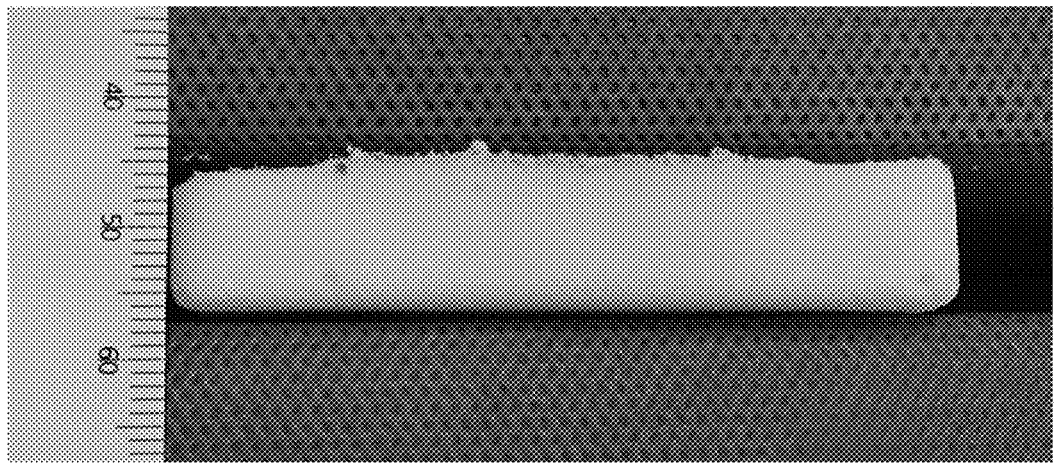
FIG. 32 is a side view of an uncompressed composition including a synthetic material coated with a biologic material, according to certain embodiments.
Figure 33:
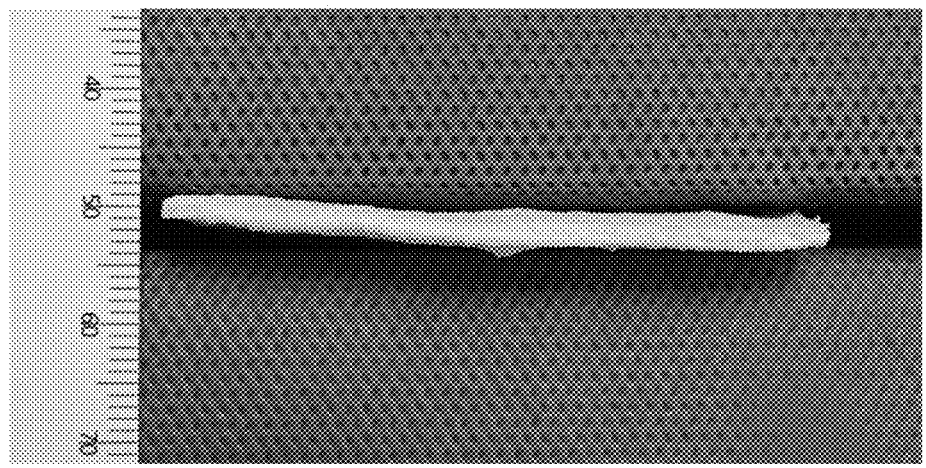
FIG. 33 is a side view of a compressed composition including a synthetic material coated with a biologic material, according to certain embodiments.

The thickness of the sponge or composition can be adjusted by modifying the thickness of the non-compressed sponge or composition, the load used for compression, the compression time, the amount of biologic material slurry used before freeze drying, or combinations thereof. As an example, the initial thickness of the freeze dried biologic material slurry can be approximately 1 cm prior to compression and can be reduced to approximately 0.25 cm after compression. For example, FIGS. 32 and 33 are side views of an uncompressed hybrid sponge and a compressed hybrid sponge.

In certain embodiments, biologic material slurry can be rubbed, coated or embedded over the synthetic material such that essentially all of the outer surfaces of the synthetic material are coated with the biologic material slurry, a predetermined amount of biologic material slurry can be poured into the bottom of a mold, the coated synthetic material can be positioned over the biologic material slurry in the mold, and a predetermined amount of biologic material slurry can be poured over the coated synthetic material. The mold can be freeze dried to form the hybrid composition. After freeze drying, the composition can be removed from the mold and a load can be imparted on the composition to compress the composition. The amount of biologic material slurry placed at the bottom of the mold and over the coated synthetic material can be selected based on the desired final thickness of the composition. For example, equal amounts of the biologic material slurry can be placed at the bottom of the mold and over the coated synthetic material to ensure that the synthetic material is in the middle of the final composition. However, the amount of biologic material slurry at the bottom of the mold can be different from the amount over the coated synthetic material if it is desired for the synthetic material to be closer to one side of the composition. Multiple compression steps can be performed by repeating the process of adding biologic material slurry to the bottom of the mold, coating the composition, adding biologic material slurry over the composition, and freeze drying the new composition prior to compression. Adding more biologic material slurry results in a thicker final composition. The desired final thickness of the composition generally dictates how much biologic material slurry is added before and after the first compression (and subsequent compressions).

Compression of the biologic material against the synthetic material embeds the biologic material into the synthetic material and results in a more dense coating of the biologic material, thereby strengthening the overall structure of the composition. Compression of the biologic material slurry against the synthetic material also stabilizes the overall shape of the composition and promotes structural stability after formation. During the freeze drying step described above, the biologic material embedded into synthetic material and forming a coating improves attachment of the biologic material slurry to the synthetic material and improves attachment of the biologic materials to each other.

In certain embodiments, the compression step can be repeated. For example, biologic material slurry can be poured to the bottom of a mold, the previously compressed composition can be coated with a subsequent layer of the biologic material slurry and placed within the mold, and biologic material slurry can be poured over the previously compressed composition. The mold can be freeze dried to form the hybrid composition. Next, the newly formed composition can be compressed against the previously compressed composition, thereby embedding or incorporating the additional biologic material into the compressed biologic material. In some embodiments, at step 116, after the compression step, the composition can be stabilized.

A predetermined amount of force can be applied during the compression stage, and a predetermined period of time of compression can be utilized. In particular, an approximately 1020 gram weight was used during an initial compression step for approximately one minute, and in a subsequent compression step an approximately 2040 gram weight was added and the composition was compressed for another minute. Approximately 25 mL of biologic material slurry was placed in the mold below the bottom of the coated synthetic material, and approximately 25 mL of biologic material slurry was placed on top of the coated synthetic material prior to freeze drying. Using such amounts of biologic material slurry resulted in a hybrid composition approximately 1 cm in height. It should be noted that the height of the hybrid composition also depends on the height of the mold. For example, the same volume of biologic material slurry produces a thinner hybrid composition in a larger mold. In certain embodiments, rather than adding additional biologic material slurry after the first compression, additional weight can be added to increase the force of compression in the second compression stage. The forces and amounts are examples only and can be varied based on the size of the samples and desired product features.

In certain embodiments, multiple compression steps can be incorporated into the process of forming the composition to add alternative materials or components (e.g., not biologic material slurry) to either side of the hybrid composition. For example, a layer of the alternative material can be placed at the bottom of a mold, the compressed composition can be placed in the mold over the alternative material, and another layer of the alternative material can be placed over the compressed composition. The mold can be placed in a freeze dryer to form a subsequent composition. After freeze drying, the composition can be removed from the mold and compressed.

In certain embodiments, at step 118, a surface coating can be added to the compressed composition. For example, the surface coating can be 100% acid-swelled biologic material slurry, gelatin, or combinations thereof. The surface coating provides for a smoother surface of the composition, resulting in no or less surface flaking of the composition.

EXAMPLES

With reference to FIGS. 2-7, front views of exemplary compositions 150 in the form of sponges having differing percentages by volume of acid-swelled biologic material (e.g., tissue) are provided. The biologic material in these experiments was formed with porcine acellular dermal matrix. Formation of the biologic material involved the steps 100-106 and step 110 as shown in FIG. 1 and as described above. In particular, the process of producing compositions with differing percentages (by volume) of acid-swelled biologic material involves the steps described below. The particle size of the biologic material was reduced. The tissue was hand cut into samples of approximately 1 inch×1 inch square tiles. The samples were fed through a meat grinder. Phosphate buffered saline (PBS) was added to the ground tissues, and the samples were further fed through a rotary cutting instrument, which was repeated 3-5 times to grind the tissues to the desired, uniform size. The ground tissues were frozen.

Next, a biologic material slurry was prepared with the processed biologic material. The pellet and a buffer were combined in a blender. The blender was pulsed to achieve a homogeneous suspension. The target solid percentage (3%) was measured with a CEM® moisture/solid analyzer. Next, the tissue underwent an acid-swell procedure. The desired percentage of the slurry to be swelled was removed (5%, 10%, etc.), centrifuged and decanted. The volume of decant supernatant was noted. A volume of acid d equal to the volume of the decanted supernatant was added, and the mixture was mixed well to resuspend the pellet. The pellet was incubated. The swelled tissue slurry was added back to the non-swelled tissue slurry, and mixed well. 20-50 mL of the mixed slurry was poured into stainless steel well molds or trays. The composition was then freeze dried. The filled stainless steel well molds were placed onto lyophilization shelves, and the material was lyophilized.

The biologic material slurry was further used in producing the synthetic-biologic hybrid compositions, as described below. In particular, the biologic material pellet was prepared using the process described above, and the biologic material slurry was prepared with the pellet. A pellet with buffer was homogenized mechanically. The target was 5% solid percentage for rubbing into the synthetic (polypropylene) mesh. The target was 3% solid percentage for use as a biologic sponge on the top and bottom of the synthetic (polypropylene) mesh. The acid-swell process was performed for both the 3% and 5% (by volume) biologic slurry. The process included removing the desired percentage of the slurry to be swelled (5%-25%), and centrifuging and decanting. The volume of decant supernatant was noted. A volume of acid equal to the volume of the decanted supernatant was added. The mixture was mixed well to resuspend the pellet and incubated. The swelled tissue slurry was added back to the non-swelled tissue slurry and mixed well.

Next, the biologic material slurry was incorporated into the synthetic material. The synthetic polypropylene mesh was cut 5 mm smaller than the stainless steel well molds. 5% solid slurry (with the desired swelled tissue percent) was incorporated into the precut synthetic polypropylene mesh by rubbing the slurry into the mesh by hand. Half of the desired total volume of the 3% slurry (with the desired swelled tissue percent) was poured into the 2 up stainless steel well mold and would become the bottom layer of the biologic sponge. The synthetic mesh containing the incorporated 5% slurry material was placed into the mold over the poured 3% slurry. Care was taken to achieve planar placement of the synthetic material over the poured 3% slurry without trapping air pockets. A wave front placement is recommended. The second half of the total volume of the 3% slurry was poured into the stainless steel well molds to create the top layer of the biologic sponge. Since a total volume of 50 mL was used, 25 mL of the slurry was poured at this stage. Next, the composition was freeze dried.

FIGS. 2-7 show Examples 1-6 of the compositions 150 including approximately 0%, 5%, 10%, 25%, 50%, and 100%, respectively, by volume of acid-swelled biologic material in the slurry used to form the composition 150, with the remainder including non-swelled biologic material. As noted above, an increase in the percentage of acid-swelled biologic material results in an increase in composition 150 stiffness. As such, the composition 150 in FIG. 2 exhibits greater flexibility than the composition 150 in FIG. 7. Each composition 150 is dimensioned as approximately two inches by two inches and has been processed to stabilize the shape. The amount of acid-swelled biologic material affects the pliability of the composition or sponge. Sponges containing an increased percentage of acid-swelled biologic material become progressively stiffer and less pliable than compositions or sponges containing less acid-swelled biologic material.

FIGS. 8-13 show magnified views of exemplary compositions including 0%, 5%, 10%, 25%, 50% and 100% acid-swelled biologic material by volume, respectively. In particular, FIGS. 8-13 show sponge collagen degradation as assessed by trichrome staining. Sponges containing up to and including 50% acid-swelled tissue by volume demonstrate minimal collagen degradation by trichrome staining. In certain embodiments, trichrome can be used to pick up degraded or damaged collagen. In contrast, degraded collagen (indicated by the arrows in FIG. 13) were clearly visible in sponges produced with 100% acid-swelled biologic material by volume.

The compositions formed by placing the biologic material slurry around the synthetic material without physically rubbing or otherwise mechanically moving the biologic material into the synthetic material, without compression of the biologic material against the synthetic material, and without formation of the smooth surfaces resulted in a weak attachment between the biologic and synthetic materials, ultimately leading to the biologic material separating and peeling away from the synthetic material. In particular, although the biologic material stayed intact around the synthetic material, the attachment between the biologic material and the synthetic material failed.

Figure 14:
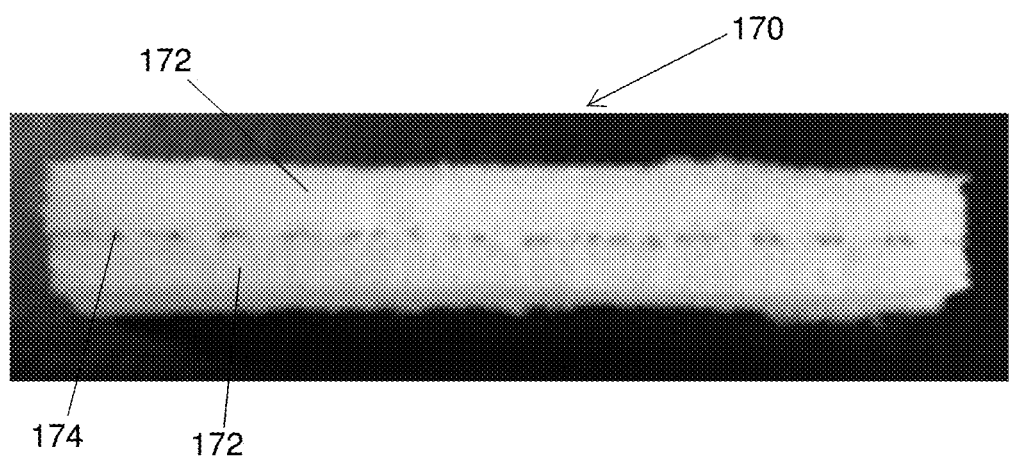
FIG. 14 is a cross-sectional view of an exemplary uncompressed composition, according to certain embodiments.
Figure 15:
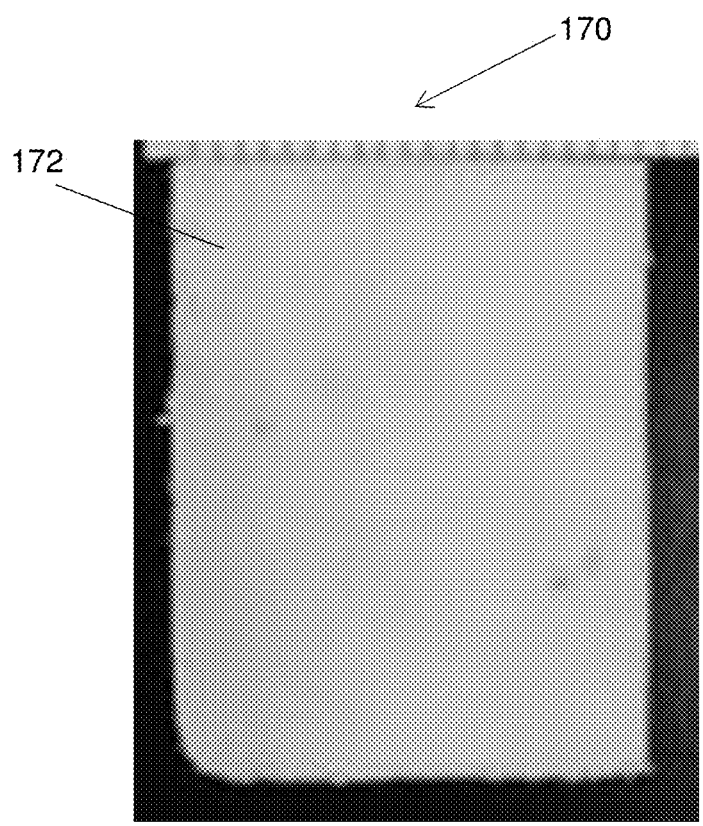
FIG. 15 is a top view of the exemplary uncompressed composition of FIG. 14, according to certain embodiments.

FIGS. 14 and 15 show cross-sectional and top views of an alternative exemplary composition 170 prototype including a biologic material 172 and a synthetic material 174 disposed between the biologic material 172 (e.g., a non-compressed hybrid sponge or composition). In certain embodiments, formation of the biologic material 172b can involve the steps 100-106 and step 110 as shown in FIG. 1 and as described above. In certain embodiments, after step 112 of FIG. 1, the hybrid sponge can be sliced on both sides up to a desired thickness while maintaining the synthetic material 174 in the middle of the hybrid sponge. Although illustrated as substantially rectangular in form, in certain embodiments, the composition 170 can be formed into a variety of configurations depending on the application of the composition 170. In certain embodiments, the configuration of the composition 170 can be determined by the mold used during formation of the composition 170. In certain embodiments, the composition 170 can be formed as substantially rectangular in configuration and can be manually trimmed or customized by a user depending on the desired application.

The composition 170 includes approximately seven percent by volume of solid content, e.g., the biologic material 172, and approximately five percent by volume of acid-swelled biologic material. In certain embodiments, the composition 170 can be formed by the process described in FIG. 1. In particular, the biologic material 172 slurry was physically rubbed or mechanically moved into the synthetic material 174 such that the biologic material 172 was forced into portions of the synthetic material 174 and created a thin coating on the outer surfaces of the synthetic material 174. The biologic material 172 was therefore incorporated into the mesh of the synthetic material 174 and created a stronger attachment between the biologic and synthetic materials 172, 174 to prevent subsequent separation of the biologic and synthetic materials 172, 174 during use. In compositions including 100% of acid-swelled biologic material 172 by volume it was found that a significant amount of force was needed to remove or separate the biologic material 172 from the synthetic material 174. In certain embodiments, rubbing of the biologic material 172 was used to remove the biologic material 172 from the synthetic material 174.

During magnified analysis of the formed compositions, interconnection between the biologic and synthetic materials 172, 174 was found to occur during the physical rubbing and/or compression stage. Such interconnection provided for a greater structural integrity of the composition by allowing the remaining biologic material 172 to encase the synthetic material 174 during the freeze drying process. In particular, rather than attaching directly to the synthetic material 174, the biologic material 172 poured or coated onto the synthetic material 174 was able to encase portions of the synthetic material 174 during the rubbing and/or compression stage.

Figure 16:
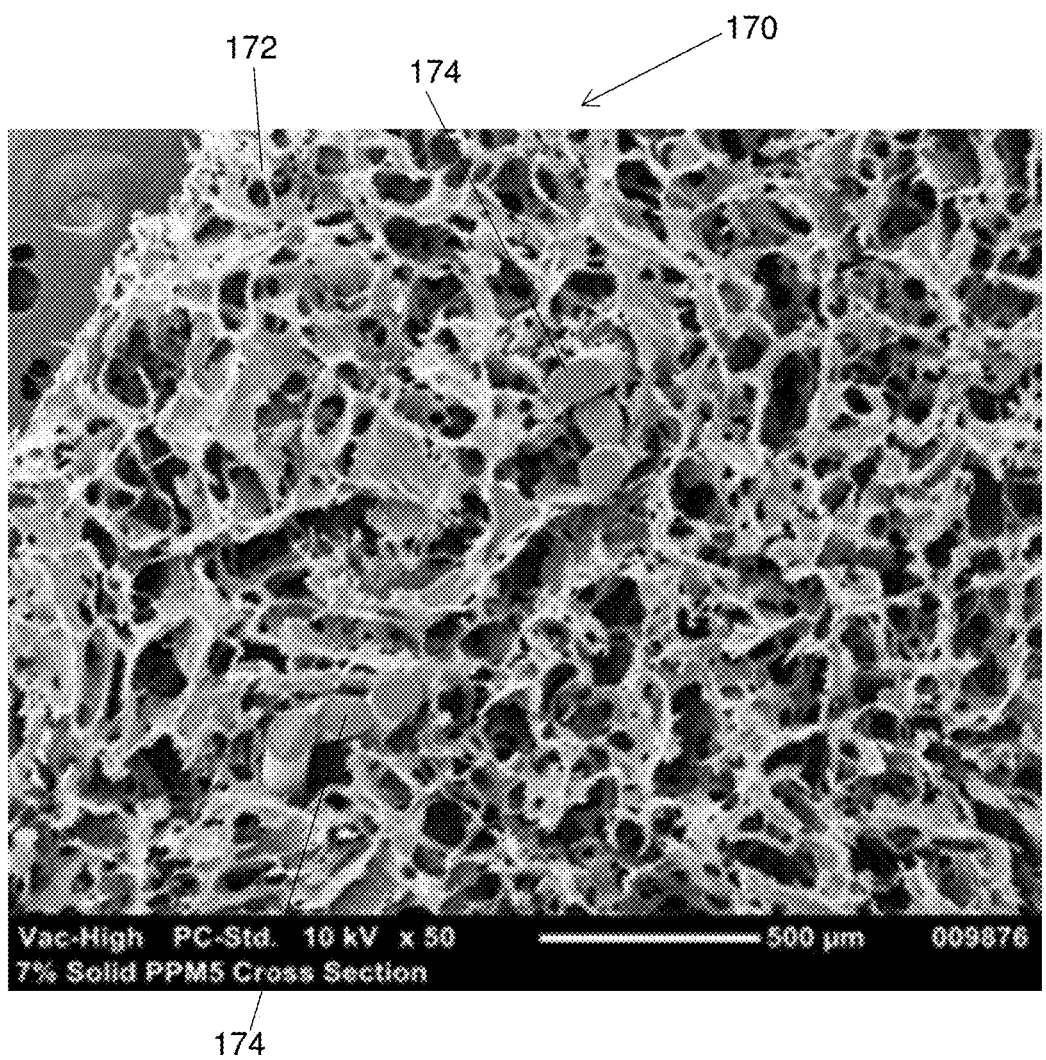
FIG. 16 is a scanning electron microscope (SEM) image of an exemplary non-compressed composition showing a synthetic material encased by a biologic material, according to certain embodiments.
Figure 17:
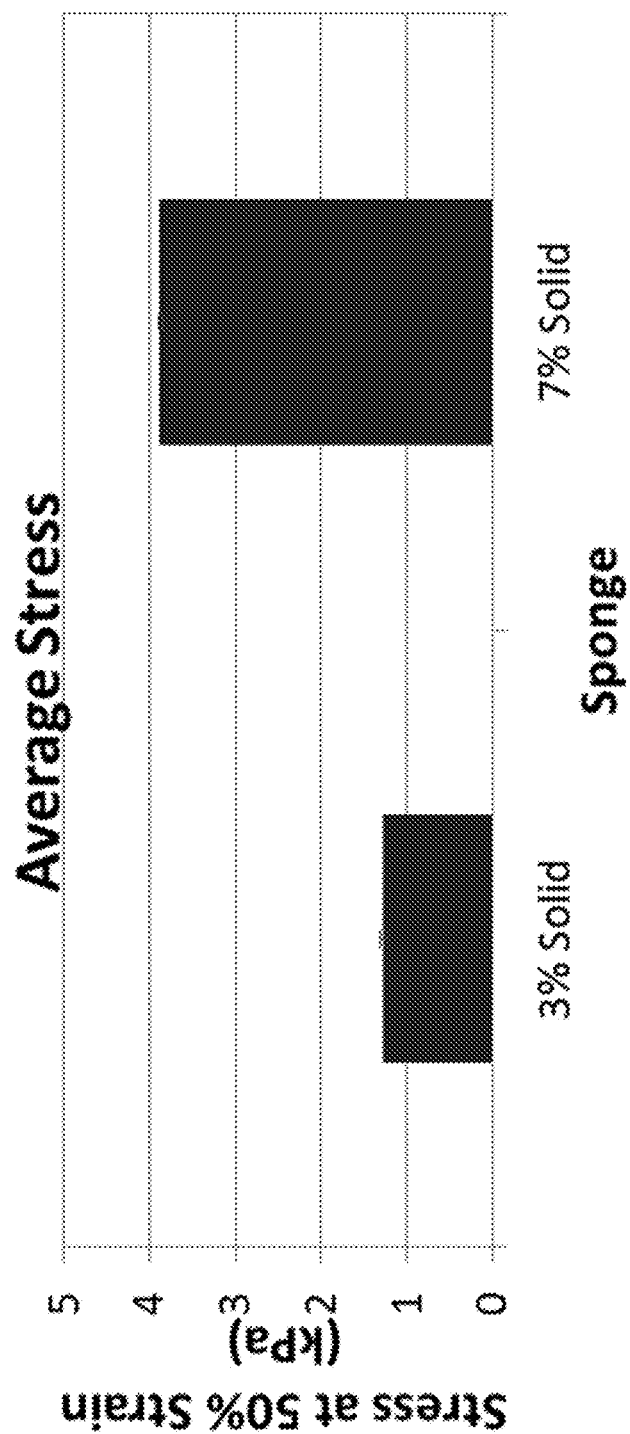
FIG. 17 is a chart of average stress at 50% strain of non-compressed exemplary compositions including 3% and 7% by volume of solid biologic material and 5% by volume of acid-swelled biologic material as a percentage of the biologic material component, according to certain embodiments.

FIG. 16 is a scanning electron microscope (SEM) image of the composition 170 of FIGS. 14 and 15 showing a synthetic material 174 encased by a biologic material 172. Experimentation was performed to determine the compression or stress values for the composition 170 at approximately 50% strain. In particular, the average stress at 50% strain of non-compressed sponges or compositions containing 3% and 7% by volume of a solid material and 5% by volume of the biologic material is provided in FIG. 17. The composition including 3% by volume of the solid material has an average stress value of approximately 1.27 kPA and the composition 170 including 7% by volume of the solid material has an average stress value of approximately 3.88 kPa. In addition, based on the results, it was determined that stress values can be modulated by varying the percentage of the biologic material in the composition.

In Vivo Rat Studies

Rat models were used for in vivo studies of the exemplary compositions discussed herein. The compositions included approximately seven percent by volume of solid biologic material and approximately five percent by volume of acid-swelled biologic material. The in vivo testing was performed to investigate the biologic response of the rat model to a polypropylene mesh as compared to a hybrid mesh composition (e.g., the biologic material physically rubbed and/or compressed into the synthetic material, and the biologic and synthetic materials molded together) when repairing an abdominal wall defect of the rat model.

Lewis rats were implemented for the experimentation. A longitudinal mid-abdominal incision was made to expose an area of the abdominal wall that measures approximately 4 cm×3 cm. A bilateral longitudinally oriented full thickness defect (approximately 4 cm×3 cm) was created in the abdominal wall by removing all tissues including membranous Scarpa's fascia, rectus muscle, the transverses fascia and peritoneum. Each abdominal wall defect was repaired with a polypropylene mesh (e.g., a control group) or a hybrid composition (e.g., 7% solid biologic material by volume, no electron beam processing—a test group) substantially equal to the size of the defect (e.g., approximately 4 cm×3 cm). In particular, the polypropylene mesh and the hybrid composition were interpositionally implanted to cover the defect in the respective rat models. The mesh and composition were implanted dry and rehydrated at the end of the procedure. Three rats were used for each type of implant. Three and six week time points were studied. Each of the rats survived for three or six weeks post implantation. After three or six weeks, the rats were euthanized and the implants, with at least 1 cm of surrounding normal tissue, were removed for gross and histological analysis.

Three Week Study

Adhesion was observed for the polypropylene only mesh (e.g., the arrow in FIG. 20) and no intestinal adhesion was observed for the hybrid mesh composition. In addition, the biologic material maintained a strong attachment to the synthetic material due to the physical rubbing and/or compression of the biologic material into the synthetic material during fabrication. Prior to implanting the polypropylene mesh and the composition, the size of the implants was approximately 4 cm in the Y direction and 3 cm in the X direction. Three weeks after implantation in the rat model, the hybrid composition contracted to approximately 3.2 cm in the Y direction and approximately 2.8 cm in the X direction. Three weeks after implantation in the rat model, the polypropylene mesh contracted to approximately 2.5 cm in both the Y and X directions (e.g., FIG. 29). The hybrid composition therefore contracted less than the polypropylene mesh alone. Therefore, the hybrid composition can maintain the overall configuration for longer periods of time to provide the requisite support to defect in the rat model post-implantation.

Gross images and hematoxylin and eosin (H&E) stained images of the polypropylene mesh and the hybrid composition after implantation in the rat model were obtained. The hybrid explant composition thickness was measured to be two or more times greater than the thickness of the polypropylene mesh explants (e.g., FIGS. 21 and 23). In addition, the polypropylene mesh showed a greater amount of inflammation than the hybrid composition (e.g., FIGS. 24 and 25). Both the polypropylene mesh and the hybrid composition had good integration with the host tissue. In particular, the hybrid composition allowed for tissue ingrowth from the host tissue. However, the implant-host interface of the polypropylene mesh included inflammation around the junction between the polypropylene mesh and the host tissue. Thus, the hybrid composition integrates with the host tissue while preventing or reducing the amount of inflammation.

The H&E stained views of the polypropylene mesh and hybrid composition three weeks after implantation in the rat model also showed that the polypropylene mesh included a greater amount of inflammation than the hybrid composition. Multiple large blood vessels formed in the hybrid composition from the tissue ingrowth (e.g., arrows in FIG. 26). Vimentin stained tissue sections of the polypropylene mesh and the hybrid composition were obtained three weeks after implantation in the rat model. Strong staining in both the polypropylene mesh and the hybrid composition indicated that several types of fibroblasts were present. It should be understood that the implants could include fibroblasts and/or myofibroblasts. The smooth muscle actin stained tissue sections of the three week polypropylene mesh and the hybrid composition explants further showed stronger staining in the polypropylene mesh, indicating that there are more myofibroblasts present in the polypropylene mesh than in the hybrid composition (e.g., FIGS. 27 and 28). The staining further shows blood vessel formation in both the polypropylene mesh and the hybrid composition.

Three Week Study Results

The three week histology study indicated advantageous properties of the hybrid composition as compared to the polypropylene mesh. In particular, the polypropylene mesh showed inflammation, greater contraction, had hematomas present, intestinal adhesion, and included a presence of fat tissue in each of the three explants. The polypropylene mesh also had only a thin layer of connective tissue surrounding the mesh. In contrast, the hybrid composition mesh included less inflammation, less contraction, no intestinal adhesions and good/healthy tissue ingrowth in each of the three explants.

Vimentin staining showed similar results of fibroblasts or myofibroblasts in both the polypropylene mesh and the hybrid composition. The SMA staining was stronger in the polypropylene mesh than the hybrid composition, indicating that more myofibroblasts were present in the polypropylene mesh than the hybrid composition. The SMA staining also correlated to the contraction observations in the polypropylene mesh. An abundance of endothelial cells was present in both the polypropylene mesh and the hybrid composition. It is further noted that the hybrid composition was dimensioned two or more times greater in thickness than the polypropylene mesh. Based on these results, the hybrid composition provides the requisite support to the defect area while reducing or preventing inflammation, and further promoting healthy tissue ingrowth.

Six Week Study

Explants of the polypropylene mesh and the hybrid composition were obtained after six weeks. No intestinal adhesion was observed for the composition. In addition, the biologic material maintained a strong attachment to the synthetic material due to the physical rubbing and/or compression of the biologic material into the synthetic material during fabrication.

The H&E stained views of the polypropylene mesh and the hybrid composition indicated that the hybrid composition thickness was two or more times greater than the thickness of the polypropylene mesh. In addition, the polypropylene mesh showed a greater amount of inflammation than the hybrid composition. Any inflammation present in the hybrid composition was concentrated around the synthetic mesh fibers. It is noted that the hybrid composition had less inflammation than the three week histology discussed above.

The H&E stained views of the polypropylene mesh and hybrid composition further showed that the polypropylene mesh had good integration with the host tissue at the implant-host interface. Although the hybrid composition had a poor implant-host interface, this was attributed to an improper surgery technique. If the surgical technique is properly performed, the implant-host interface of the hybrid composition is expected to have strong and healthy tissue ingrowth, as well as low inflammation levels.

The H&E stained views of the polypropylene mesh and hybrid composition showed that the polypropylene mesh container a large amount of inflammation while the hybrid composition contained minimial inflammation with the inflammation mainly centered around the synthetic fibers. Multiple blood vessels formed in the polypropylene mesh due to inflammation, while multiple blood vessels formed in the hybrid composition due to tissue ingrowth. Overall, the hybrid composition at six weeks had less inflammation and a denser tissue matrix than either the polypropylene mesh at six weeks or the hybrid composition at three weeks.

Smooth muscle actin (SMA) stained tissue sections of the polypropylene mesh and the hybrid composition were obtained six weeks after implantation in the rat abdominal wall model. The stronger staining in the polypropylene mesh indicated that there are more myofibroblasts present in the polypropylene mesh than in the hybrid composition. The staining further showed an abundance of blood vessel formation in the hybrid composition, indicating strong tissue ingrowth and integration with the host tissue.

Six Week Study Results

The six week histology study indicated advantageous properties of the hybrid composition as compared to the polypropylene mesh. In particular, the polypropylene mesh showed a persistence in inflammation from the three week explant, the presence of hematomas, fat tissue lining the inner portion of the polypropylene mesh, and a thin layer of connective tissue surrounding the polypropylene mesh in each of the three explants. In contrast, the hybrid composition included a reduction in inflammation as compared to the three week explant (except for slight inflammation around the synthetic fibers), showed a strong cellular response and tissue ingrowth (e.g., abundant vessels present, a dense matrix as compared to the three week explant, and the like), and remained dimensioned more than two times thicker than the polypropylene mesh.

Based on these results, the hybrid composition retained the tensile strength of the synthetic material or mesh throughout processing. The hybrid composition also induced a better biologic response than the uncoated polypropylene mesh. The hybrid composition therefore promoted tissue ingrowth, reduced organ adhesion, reduced contraction, and reduced inflammation. Thus, the hybrid composition provides an improved biologic response post-implantation and retains a strong attachment between the synthetic and biologic materials over time.

Figure 20:
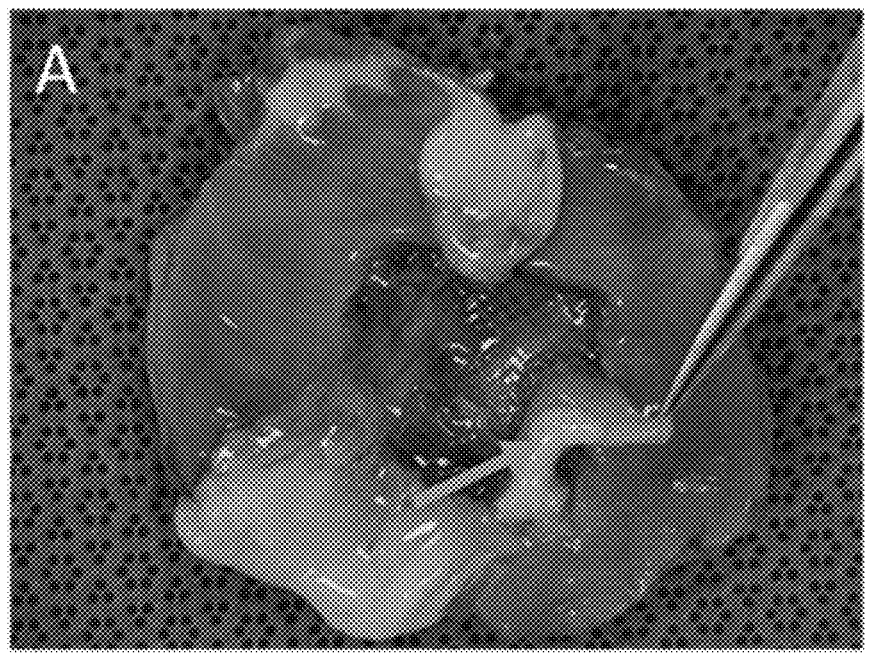
FIG. 20 is a gross image of an explant of a composition including a synthetic mesh, showing a rat abdominal wall defect treated with the composition, with an arrow showing tissue adhesion to the synthetic mesh, according to certain embodiments.
Figure 21:
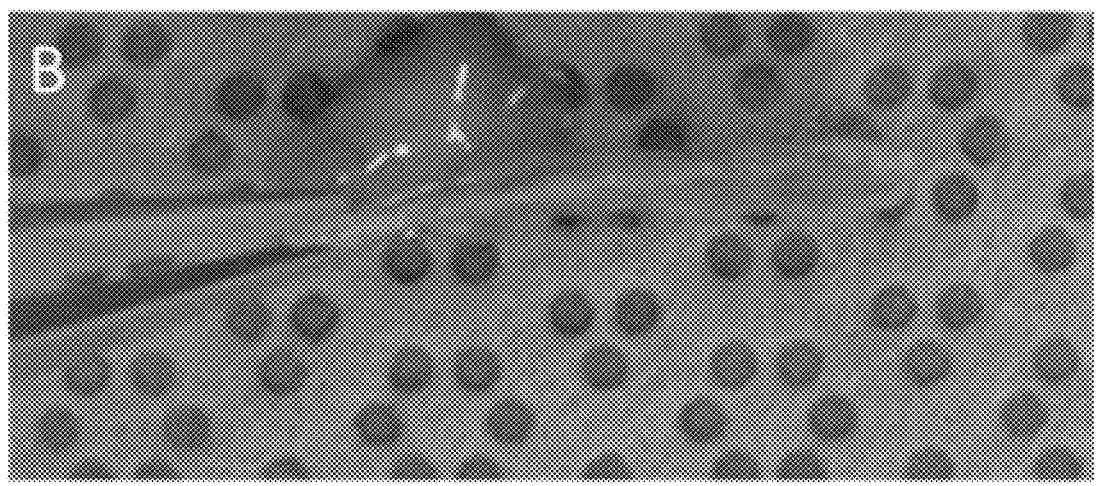
FIG. 21 is a gross image of a cross-section of an explant of a composition including a synthetic mesh used to treat a defect in a rat abdominal wall, according to certain embodiments.
Figure 22:
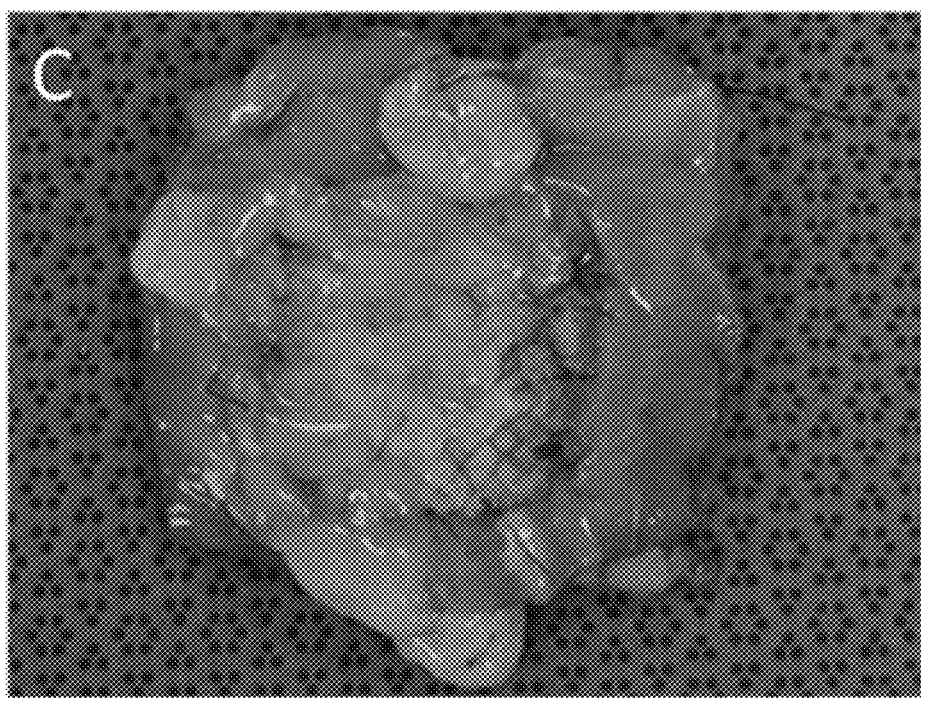
FIG. 22 is a gross image of a non-compressed composition explant including a synthetic material coated with a biologic material, showing a rat abdominal wall defect treated with the non-compressed composition, according to certain embodiments.
Figure 23:
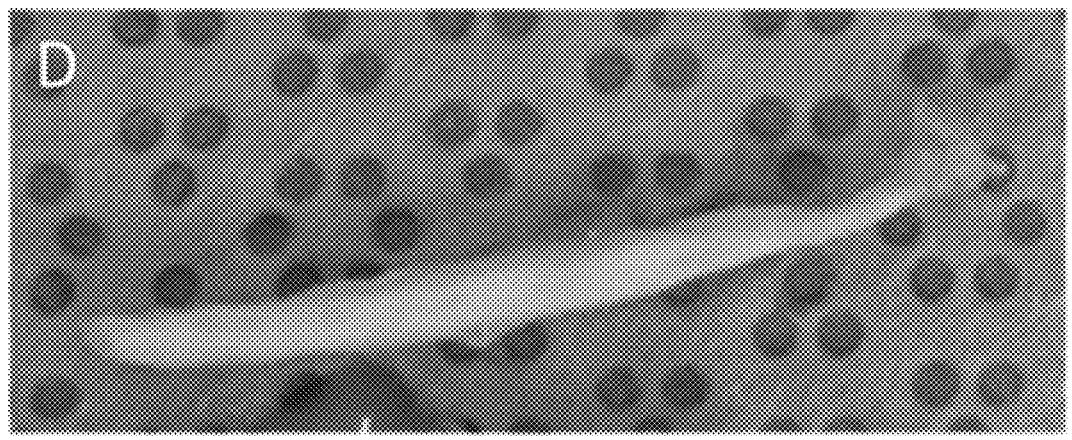
FIG. 23 is a gross image of a cross-section of a non-compressed composition explant including a synthetic material coated with a biologic material, used to treat a defect in a rat abdominal wall, according to certain embodiments.

FIGS. 20 and 21 show gross images of a synthetic mesh explant and FIGS. 22 and 23 show a non-compressed hybrid sponge or composition explant. The synthetic mesh and the non-compressed hybrid composition were used to repair a defect in the rat abdominal wall. FIG. 20 shows a defect repaired with the synthetic mesh and FIG. 22 shows a defect repaired with the non-compressed composition, while FIG. 21 shows a cross-sectional image of the explanted synthetic mesh and FIG. 23 shows a cross-sectional image of the explanted non-compressed composition. The explanted synthetic mesh defines a thinner width than the non-compressed composition. In addition, intestinal adhesions (shown by the arrow in FIG. 20) to the synthetic mesh were observed in 33% of defects repaired with the synthetic mesh. No adhesions were observed in defects repaired with the non-compressed compositions.

Figure 24:
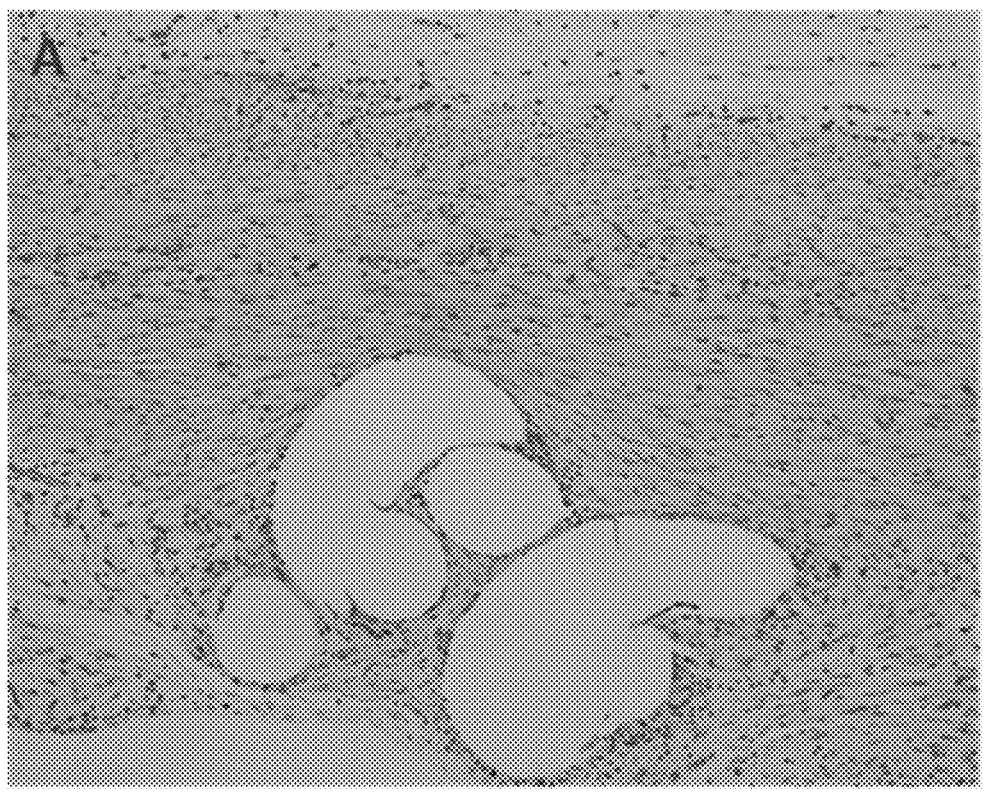
FIG. 24 is a hematoxylin and eosin (H&E) stained image of an explant of a rat abdominal wall defect treated with a polypropylene mesh without a biologic material coating, according to certain embodiments.
Figure 25:
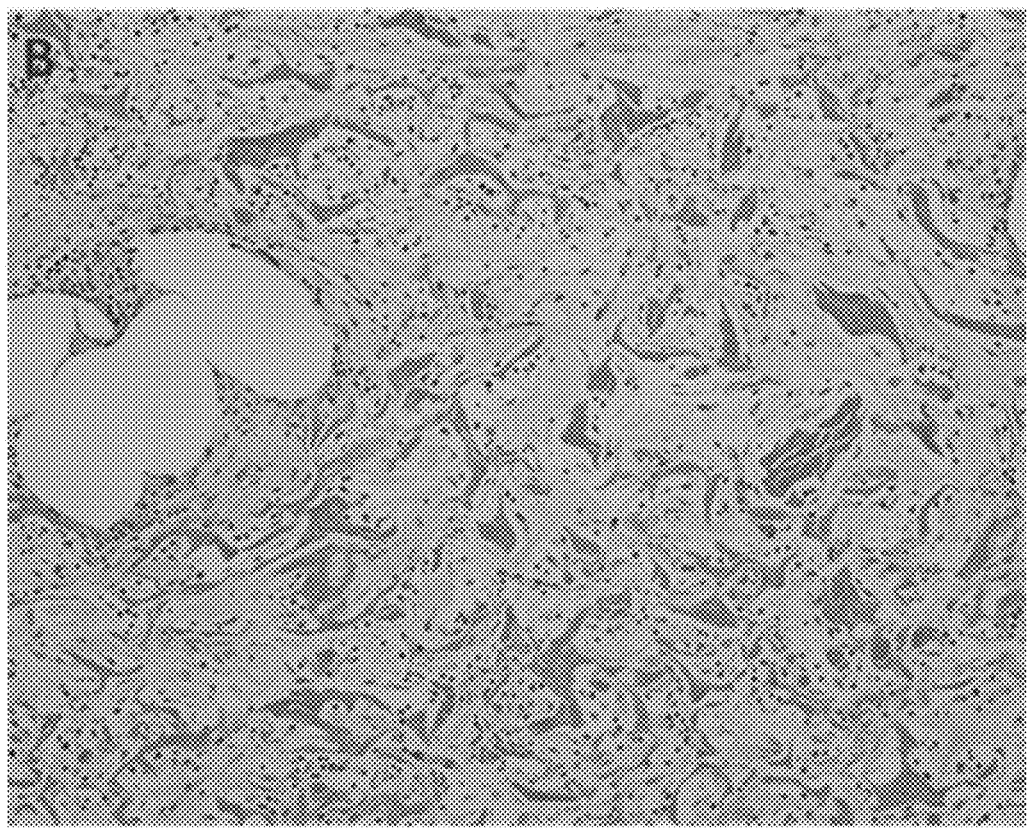
FIG. 25 is a hematoxylin and eosin (H&E) stained image of an explant from a rat abdominal wall defect treated with a non-compressed composition including a synthetic material coated with a biologic material, according to certain embodiments.
Figure 26:
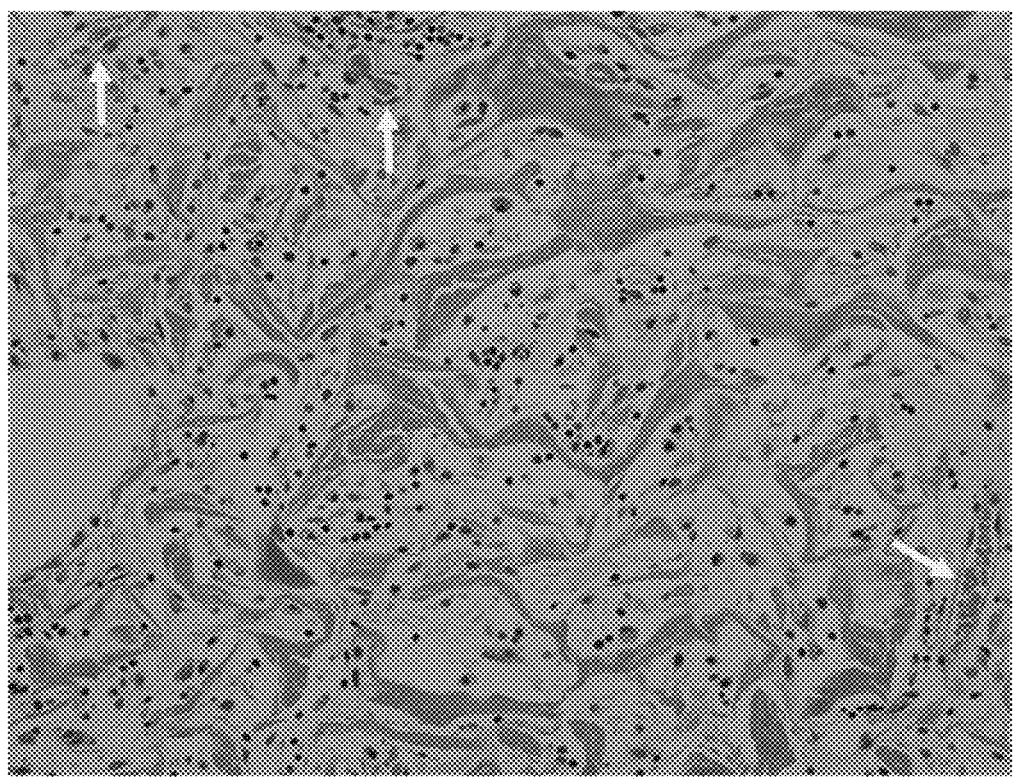
FIG. 26 is a hematoxylin and eosin (H&E) stained section showing blood vessels visible in a non-compressed composition explant including a synthetic material coated with a biologic material, according to certain embodiments.

FIG. 24 is a hematoxylin and eosin (H&E) image of an explant of a rat abdominal wall defect repaired with a synthetic mesh, and FIG. 25 is an H&E image of an explant of a rat abdominal wall defect repaired with a non-compressed composition. The synthetic mesh explants showed a multitude of inflammatory cells surrounding the synthetic material as well as throughout the rest of the repaired area. The non-compressed composition explants showed minimal inflammation around the synthetic material with even and abundant infiltration of fibroblast-like cells throughout the rest of the repaired areas. FIG. 26 is an H&E image showing blood vessels visible in a non-compressed composition explant. In particular, the arrows in FIG. 26 show the abundant blood vessels formed and visible in the non-compressed composition explant.

Figure 27:
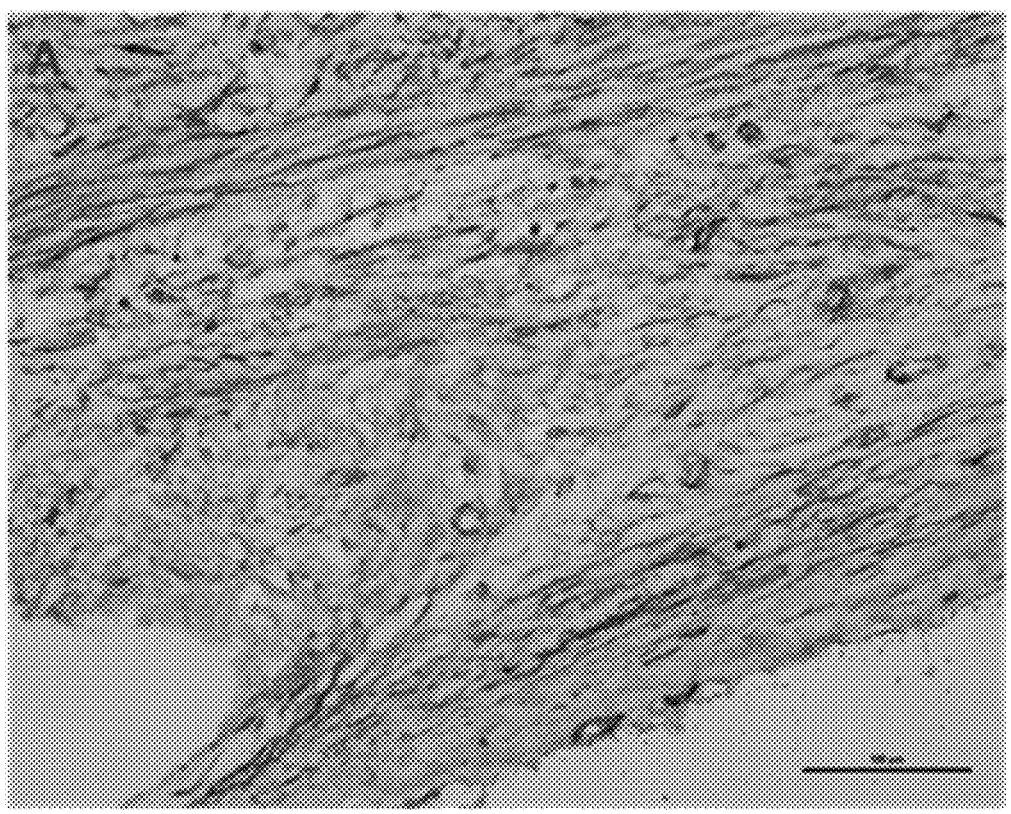
FIG. 27 is a smooth muscle actin (SMA) stained section of an explant from a rat abdominal wall defect treated with a polypropylene mesh without a biologic material coating, according to certain embodiments.
Figure 28:
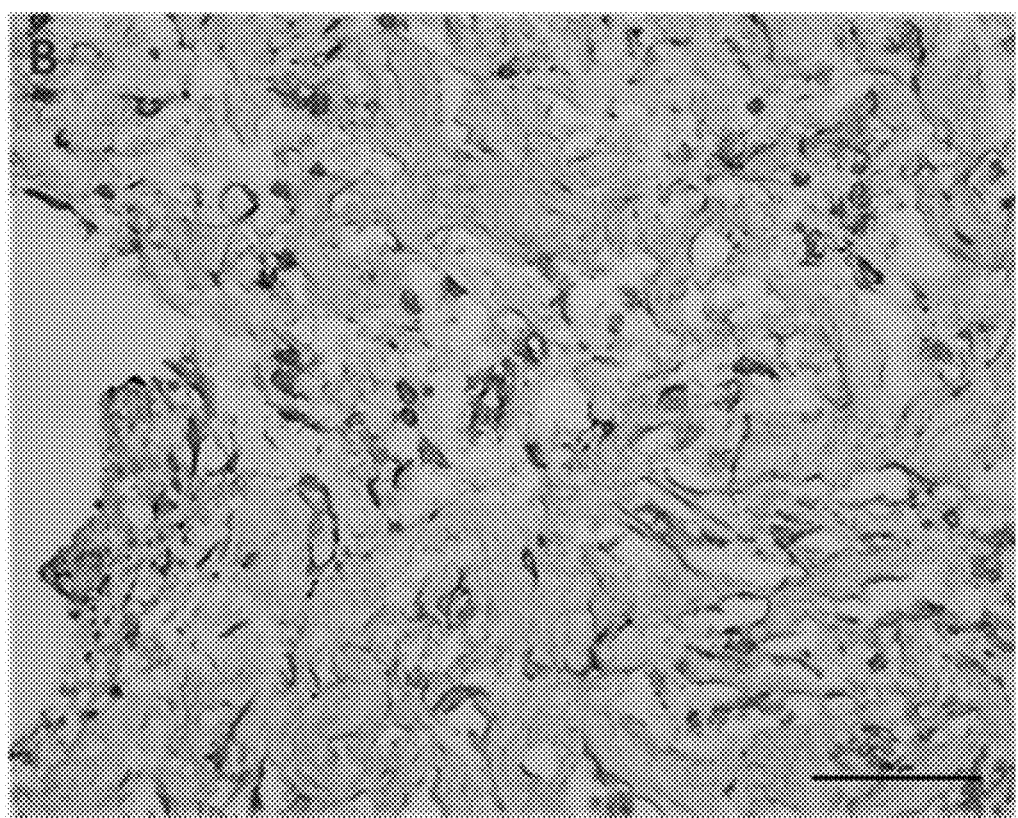
FIG. 28 is a smooth muscle actin (SMA) stained image of an explant from rat abdominal wall defect treated with a non-compressed composition including a synthetic material coated with a biologic material, according to certain embodiments.

FIG. 27 shows a smooth muscle actin (SMA) stain of an explant of a rat abdominal wall defect repaired with a synthetic mesh—and FIG. 28 is an SMA stain of an explant of a rat abdominal wall defect repaired with a non-compressed composition. SMA is present in both myofibroblasts and endothelial cells. The synthetic mesh explant of FIG. 27 shows an abundance of SMA containing cells, many of which also align (in a diagonal direction), indicating a strong presence of myofibroblasts. Some blood vessels are also present as shown by the circular brown staining. The hybrid non-compressed composition of FIG. 28 shows sparse and localized areas of SMA containing cells, indicating a lack of myofibroblasts and presence of blood vessels.

Figure 29:
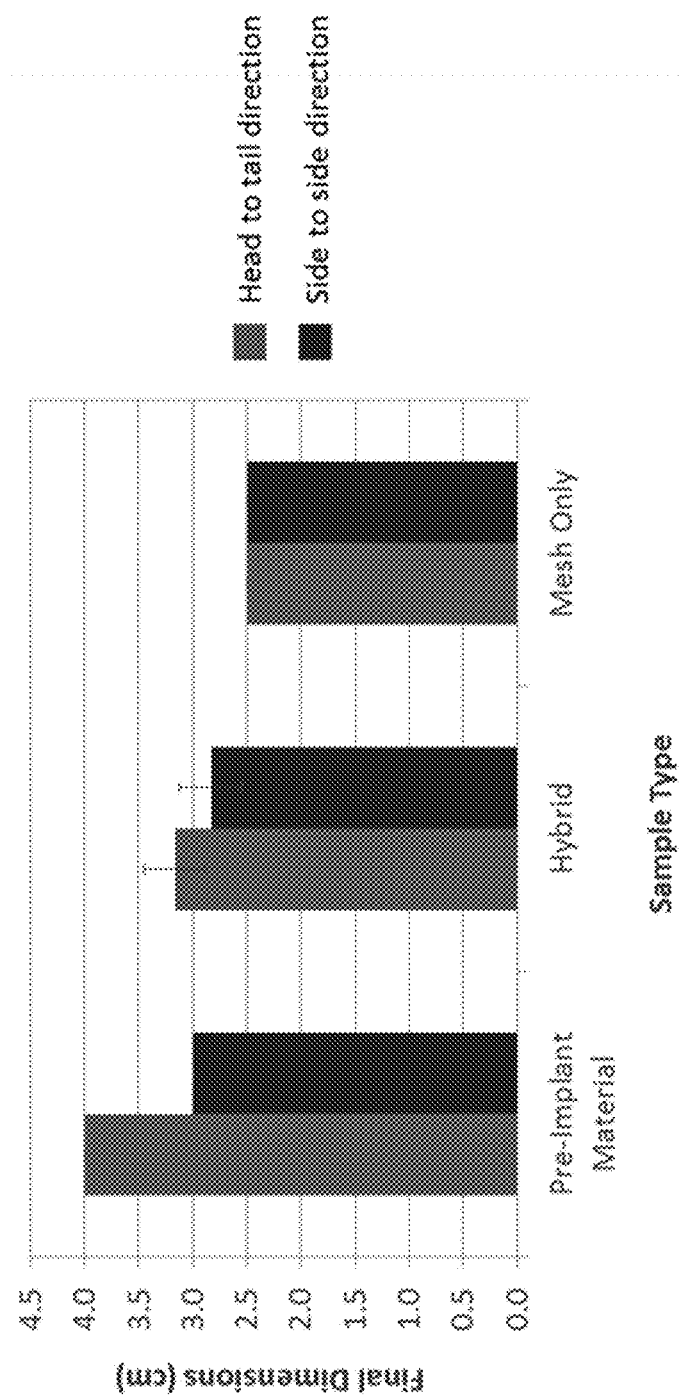
FIG. 29 is a chart of a size of an original rat abdominal wall defect and a rat abdominal wall defect treated with a polypropylene mesh without a biologic material coating and a non-compressed composition including a synthetic material coated with a biologic material, according to certain embodiments.

FIG. 29 is a chart of a size of an original rat abdominal wall defect and a repaired rat abdominal wall defect for defects repaired with a synthetic mesh and a non-compressed composition. The bar on the left for each material indicates the head to tail direction measurement, while the bar on the right for each material indicates the side to side direction measurement of the abdominal wall defect. The data of FIG. 29 indicates that the pre-implant material or original abdominal wall defect has the greatest measurements, the hybrid non-compressed composition has the next lowest measurements, and the synthetic mesh has the lowest measurements for the repaired abdominal wall defect. Defects repaired with synthetic mesh alone contracted more and became smaller than those repaired with hybrid non-compressed compositions. This data was found to be consistent with the SMA staining data which showed more myofibroblasts (cells responsible for contraction) in the synthetic mesh explant than the hybrid non-compressed composition explant.

Figure 18:
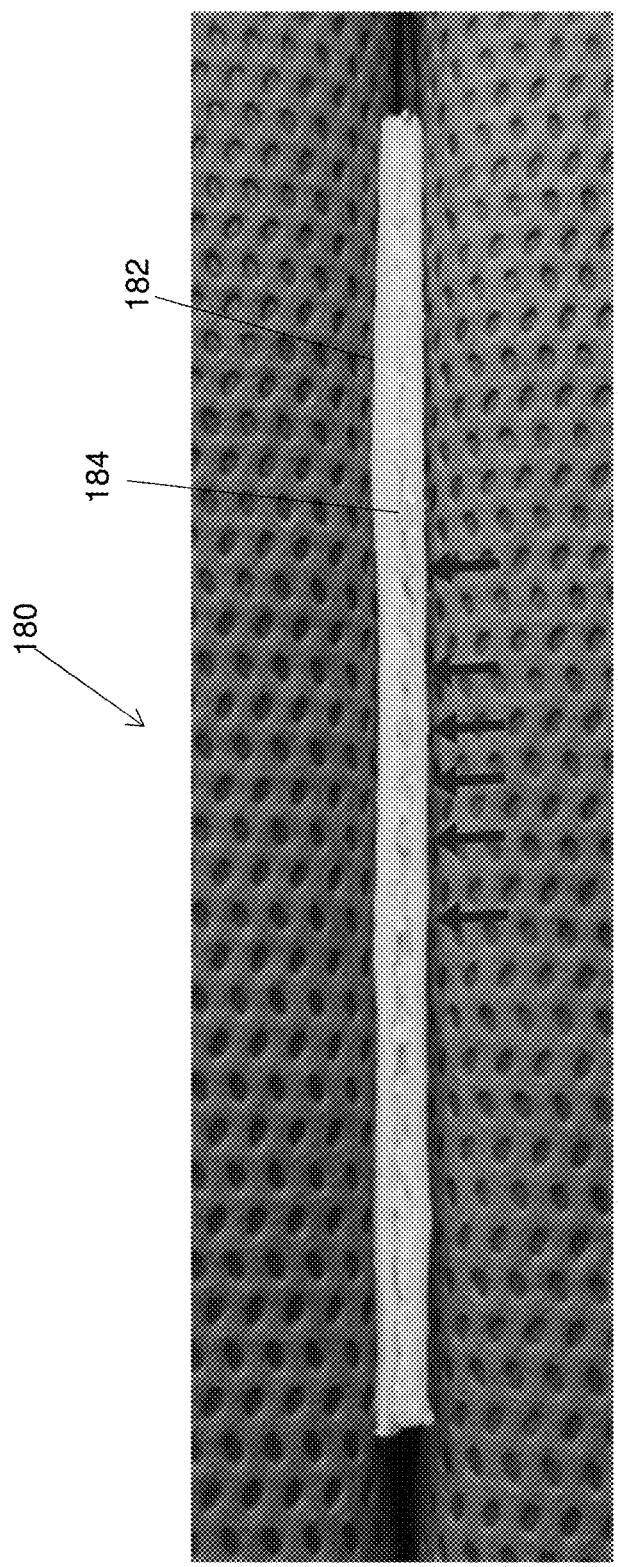
FIG. 18 is a cross-sectional view of an exemplary compressed composition including a synthetic material encased by a biologic material, according to certain embodiments.
Figure 19:
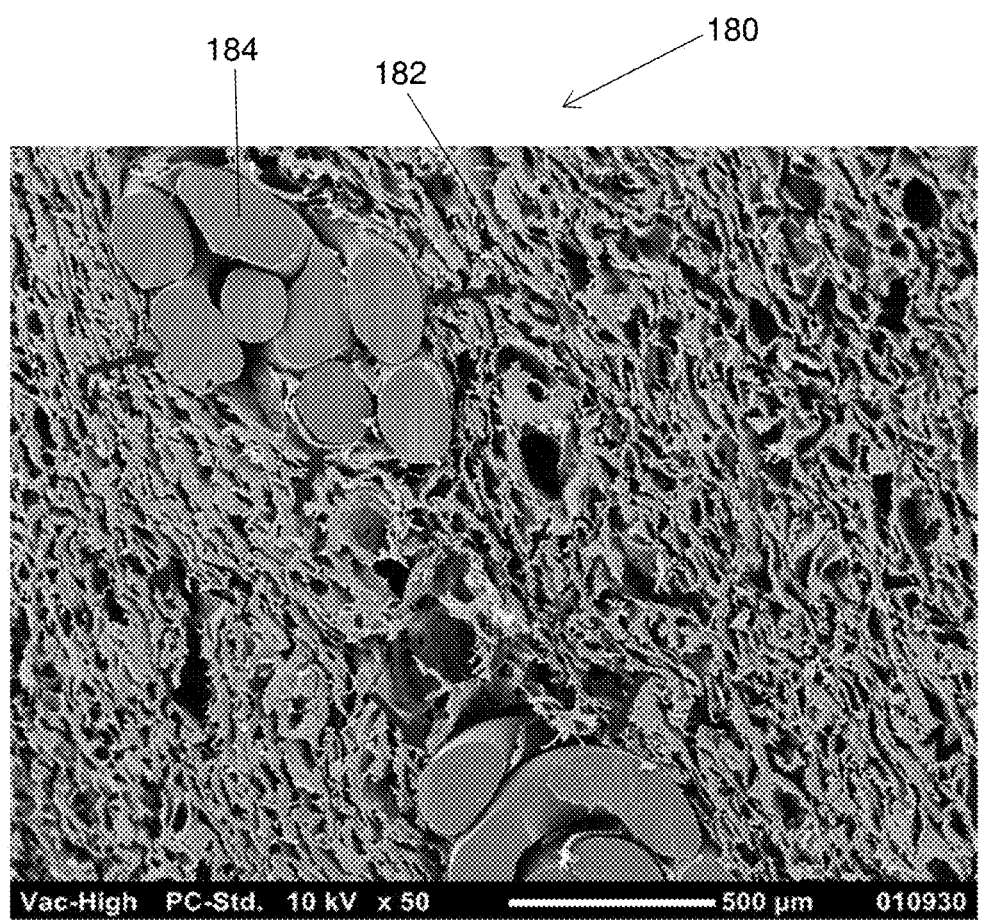
FIG. 19 is a scanning electron microscope (SEM) image of an exemplary compressed composition showing a synthetic material encased by a biologic material, according to certain embodiments.

FIG. 18 is a cross-sectional view of an exemplary compressed hybrid sponge or composition 180. The composition 180 includes a synthetic material 184 disposed between and compressed by the biologic material 182. FIG. 19 is an SEM image of the compressed composition 180 showing the synthetic material 184 encased by the biologic material 182.

Figure 30:
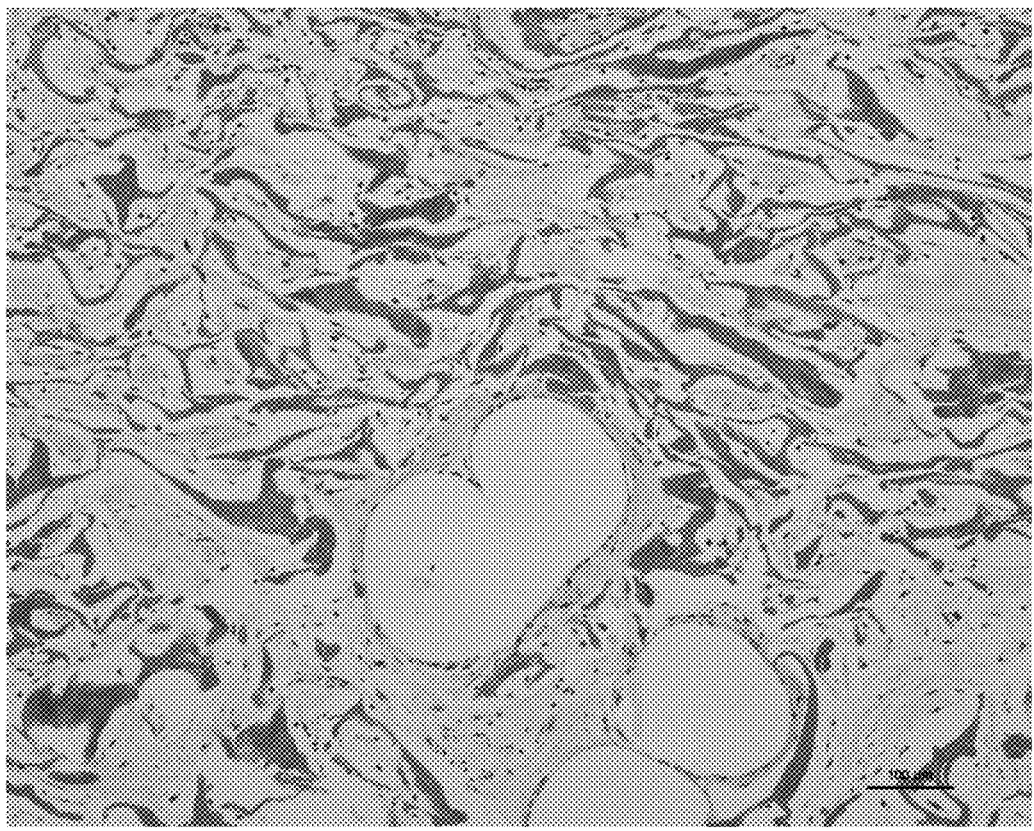
FIG. 30 is a hematoxylin and eosin (H&E) stained image showing compressed compositions including a synthetic material coated with a biologic material implanted in a rat subcutaneous space for four weeks, according to certain embodiments.

FIG. 30 is an H&E image showing compressed compositions implanted in a rat subcutaneous space for four weeks. The compressed hybrid sponge or composition showed minimal inflammation around the synthetic material with even and abundant infiltration of fibroblast-like cells and vessels throughout the rest of the repaired areas, similar to the biologic response to the non-compressed compositions. This data suggests that compression does not adversely affect the biologic response.

The bio-synthetic hybrid composition provides a surgical three-dimensional scaffold for tissue repair, attachment, reinforcement, reconstruction, or combinations thereof, which advantageously minimizes complications and promotes tissue ingrowth, leading to an overall improved surgical outcome. The inherent biomechanical strength due to the synthetic material or component (absorbable or non-absorbable) can be on several orders of magnitude higher than the biologic material alone. The biologic material or component can be manufactured to any shape, size, porosity, or stiffness, while maintaining the biological advantages associates with biologic materials (e.g., rapid revascularization, cell repopulation, white cell migration, or combinations thereof). Therefore, the exemplary compositions can be used in a wide array of applications, such as trocar, laparoscopic, hemostat, hernia, abdominal wall, soft tissue repair, fistula, pelvic organ prolapse, or hysterectomy.

Although the compositions and methods of the present disclosure have been described with reference to exemplary embodiments thereof, the present disclosure is not limited to such exemplary embodiments and or implementations. Rather, the compositions and methods of the present disclosure are susceptible to many implementations and applications, as will be readily apparent to persons skilled in the art from the disclosure hereof. The present disclosure expressly encompasses such modifications, enhancements and or variations of the disclosed embodiments. Since many changes could be made in the above exemplary embodiments and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A method of producing a surgical material, comprising:
providing a synthetic material substrate;
selecting a collagen-containing tissue matrix;
creating a slurry with the collagen-containing tissue matrix, wherein creating the slurry comprises:
subjecting a portion of the collagen-containing tissue matrix to an acid swelling process to produce an acid-swelled tissue matrix, resulting in (i) the acid-swelled tissue matrix including the portion of the collagen-containing tissue matrix and (ii) a remainder portion of the collagen-containing tissue matrix; and
mixing the acid-swelled tissue matrix with the remainder portion of the collagen-containing tissue matrix to produce a slurry having between 5% and 35% by volume of the acid-swelled tissue matrix; and
embedding the synthetic material substrate in the slurry.

2. The method of claim 1, wherein the slurry has between 5% and 25% by volume of the acid-swelled tissue matrix.

3. The method of claim 1, wherein the slurry has between 5% and 10% by volume of the acid-swelled tissue matrix.

4. The method of claim 1, wherein the acid swelling process comprises suspending the portion of the collagen-containing tissue matrix in acid and incubating the portion of the collagen-containing tissue matrix in the acid until swelling occurs.

5. The method of claim 1, comprising performing a decellularization process for the collagen-containing tissue matrix.

6. The method of claim 1, comprising resuspending the slurry in a buffer.

7. The method of claim 1, comprising incorporating an antimicrobial compound into the surgical material.

8. The method of claim 1, comprising incorporating an anti-inflammatory compound into the surgical material.

9. The method of claim 1, wherein the synthetic material substrate comprises at least one of a porous foam, a planar mesh, a monofilament woven material, a multifilament woven material, multi-leveled layers, or multi-directional layers.

10. The method of claim 1, wherein a tensile strength of the synthetic material substrate is greater than a tensile strength of the collagen-containing tissue matrix.

11. The method of claim 1, wherein the synthetic material substrate comprises textured surfaces.

12. The method of claim 1, wherein the collagen-containing tissue matrix comprises an acellular tissue matrix.

13. The method of claim 1, comprising processing the collagen-containing tissue matrix to produce a group of collagen-containing tissue matrix fragments, at least a portion of the collagen-containing tissue matrix fragments including frayed ends.

14. The method of claim 1, comprising pouring a portion of the slurry into a mold to cover a bottom of the mold with the slurry, positioning the synthetic material substrate coated with the slurry into the mold on the slurry, pouring the slurry over the synthetic material substrate positioned in the mold to cover the synthetic material substrate, and freeze drying the surgical material to combine the collagen-containing tissue matrix and the synthetic material substrate.

15. The method of claim 1, comprising freeze drying the synthetic material substrate and at least the portion of the slurry to form the surgical material, wherein freeze drying the synthetic material substrate and at least the portion of the slurry produces a smooth layer or skin on an outer surface of the surgical material.

16. The method of claim 15, further comprising compressing the portion of the slurry and the synthetic material substrate after freeze drying.

17. The method of claim 1, wherein embedding the synthetic material substrate in the slurry comprises mechanically forcing, moving or rubbing at least a portion of the slurry into the synthetic material substrate.

18. The method of claim 17, wherein mechanically forcing, moving or rubbing at least the portion of the slurry into the synthetic material substrate forces the portion of the slurry into openings in an outer surface of the synthetic material substrate.

19. The method of claim 16, wherein compressing the portion of the slurry and the synthetic material substrate embeds the slurry into the synthetic material substrate.

* * * * *